United States Patent
Nguyen et al.

(10) Patent No.: US 9,033,133 B2
(45) Date of Patent: May 19, 2015

(54) METHOD AND APPARATUS FOR CONVEYING A CELLULOSIC FEEDSTOCK

(75) Inventors: Quang A. Nguyen, Chesterfield, MO (US); Sunalie N. Hillier, Georgetown (CA); Murray J. Burke, Oakville (CA)

(73) Assignee: Abengoa Bioenergy New Technologies, LLC., Chesterfield, MO (US)

( * ) Notice: Subject to any disclaimer, the term of this patent is extended or adjusted under 35 U.S.C. 154(b) by 411 days.

(21) Appl. No.: 12/361,103

(22) Filed: Jan. 28, 2009

(65) Prior Publication Data
US 2010/0186735 A1 Jul. 29, 2010

(30) Foreign Application Priority Data
Jan. 23, 2009 (CA) ................................. 2650919

(51) Int. Cl.
| | |
|---|---|
| B65G 33/18 | (2006.01) |
| C13K 1/02 | (2006.01) |
| C08H 8/00 | (2010.01) |
| C12M 1/00 | (2006.01) |
| C12M 1/33 | (2006.01) |
| C12P 7/10 | (2006.01) |
| D21C 11/00 | (2006.01) |

(52) U.S. Cl.
CPC ...... *C12P 7/10* (2013.01); *C08H 8/00* (2013.01); *C12M 21/12* (2013.01); *C12M 45/02* (2013.01); *C12M 45/06* (2013.01); *C12M 45/20* (2013.01); *C12P 2201/00* (2013.01); *D21C 11/0007* (2013.01); *Y02E 50/16* (2013.01)

(58) Field of Classification Search
None
See application file for complete search history.

(56) References Cited

U.S. PATENT DOCUMENTS

| | | |
|---|---|---|
| 319,299 A | 6/1885 | Morgan |
| 459,113 A | 9/1891 | Rymal |
| 1,073,425 A | 9/1913 | Lambert |
| 1,106,736 A | 8/1914 | Schuller |
| 1,173,825 A | 2/1916 | McWallen |
| 1,190,923 A | 7/1916 | Lindquist |
| 1,247,153 A | 11/1917 | Roberts |
| 1,560,855 A | 11/1925 | Queneau |
| 1,824,221 A | 9/1931 | Mason |
| 2,080,327 A | 5/1937 | McKinnis |
| 2,086,701 A | 7/1937 | Dreyfus |

(Continued)

FOREIGN PATENT DOCUMENTS

| | | |
|---|---|---|
| CA | 1070537 | 1/1980 |
| CA | 1096374 B | 2/1981 |

(Continued)

OTHER PUBLICATIONS

International Search Report received in connection to the co-pending international patent application No. PCT/CA2010/000087, mailed on May 4, 2010.

(Continued)

*Primary Examiner* — Kavel Singh
(74) *Attorney, Agent, or Firm* — Armstrong Teasdale LLP

(57) ABSTRACT

A method and apparatus for preparing a cellulosic feedstock are disclosed. Embodiments of the method comprise passing the cellulosic feedstock out of at least one outlet of a vessel (such as a holding tank) and obtaining at least two streams of cellulosic feedstock wherein each stream may be fed different hydrolysis reactors. Embodiments of the apparatus comprise passing the cellulosic feedstock downwardly through the vessel and withdrawing the feedstock from the vessel in two different lateral directions.

13 Claims, 10 Drawing Sheets

(56) References Cited

U.S. PATENT DOCUMENTS

| | | |
|---|---|---|
| 2,263,608 A | 11/1941 | Brown |
| 2,333,739 A | 11/1943 | Puckett |
| 2,541,058 A | 2/1951 | Heritage et al. |
| 2,541,059 A | 2/1951 | Heritage et al. |
| 2,541,127 A | 2/1951 | Van Beckum |
| 2,570,042 A | 10/1951 | West |
| 2,595,827 A | 5/1952 | Boruff et al. |
| 2,615,883 A | 10/1952 | Sweeney et al. |
| 2,697,703 A | 12/1954 | Heritage et al. |
| 2,758,031 A | 8/1956 | Ozai-Durrani |
| 3,017,404 A | 1/1962 | Ball |
| 3,109,560 A | 11/1963 | Rosenleaf |
| 3,199,731 A * | 8/1965 | Brauer et al. ............... 222/56 |
| 3,223,697 A | 12/1965 | Ball et al. |
| 3,357,437 A | 12/1967 | Maguire |
| 3,383,277 A | 5/1968 | Gordon et al. |
| 3,407,943 A | 10/1968 | Douglass, Jr. |
| 3,572,593 A | 3/1971 | Guarisco |
| 3,617,433 A | 11/1971 | Sutherland |
| 3,640,509 A | 2/1972 | Inamura et al. |
| 3,743,572 A | 7/1973 | Richter et al. |
| 3,817,826 A | 6/1974 | Hoye |
| 3,964,874 A | 6/1976 | Maruko et al. |
| 3,964,880 A | 6/1976 | Siegrist |
| 4,023,982 A | 5/1977 | Knaugh |
| 4,055,673 A | 10/1977 | Mueller et al. |
| 4,062,304 A | 12/1977 | Herbold et al. |
| 4,119,025 A | 10/1978 | Brown |
| 4,136,207 A | 1/1979 | Bender |
| 4,160,695 A | 7/1979 | Dietrichs et al. |
| 4,181,796 A | 1/1980 | Dietrichs et al. |
| 4,186,658 A | 2/1980 | Brown |
| 4,196,827 A | 4/1980 | Leafdale |
| 4,200,692 A | 4/1980 | Puls et al. |
| 4,211,163 A | 7/1980 | Brown et al. |
| 4,237,226 A | 12/1980 | Grethlein |
| 4,281,934 A | 8/1981 | Krause |
| 4,286,884 A | 9/1981 | Retrum |
| 4,296,864 A | 10/1981 | Misaka et al. |
| 4,316,748 A | 2/1982 | Rugg et al. |
| 4,331,447 A | 5/1982 | Kamada et al. |
| 4,341,353 A | 7/1982 | Hamilton et al. |
| 4,364,667 A | 12/1982 | Reiner |
| 4,412,485 A | 11/1983 | Brown |
| 4,427,453 A | 1/1984 | Reitter |
| 4,432,805 A * | 2/1984 | Nuuttila et al. ............... 127/37 |
| 4,436,586 A | 3/1984 | Elmore |
| 4,451,567 A | 5/1984 | Ishibashi et al. |
| 4,461,648 A | 7/1984 | Foody |
| 4,470,851 A | 9/1984 | Paszner et al. |
| 4,483,625 A | 11/1984 | Fisher et al. |
| 4,511,433 A | 4/1985 | Tournier et al. |
| 4,584,057 A | 4/1986 | Rowe et al. |
| 4,600,590 A | 7/1986 | Dale |
| 4,615,742 A * | 10/1986 | Wright ............... 127/37 |
| 4,645,541 A | 2/1987 | Delong |
| 4,667,373 A | 5/1987 | Roder |
| 4,670,944 A | 6/1987 | Thrash |
| 4,676,363 A | 6/1987 | Buchmuller et al. |
| 4,746,404 A | 5/1988 | Laakso |
| 4,751,034 A | 6/1988 | Delong et al. |
| 4,752,579 A | 6/1988 | Arena et al. |
| 4,764,596 A | 8/1988 | Lora et al. |
| 4,775,239 A | 10/1988 | Martinek et al. |
| 4,798,651 A | 1/1989 | Kokta |
| 4,867,846 A | 9/1989 | Fleck |
| 4,869,786 A | 9/1989 | Hanke |
| 4,908,098 A | 3/1990 | Delong et al. |
| 4,908,099 A | 3/1990 | Delong |
| 4,911,558 A | 3/1990 | Teske |
| 4,947,743 A | 8/1990 | Brown et al. |
| 4,966,650 A | 10/1990 | Delong et al. |
| 4,997,488 A | 3/1991 | Gould et al. |
| 5,012,731 A * | 5/1991 | Maisonneuve ............... 100/110 |
| 5,023,097 A | 6/1991 | Tyson et al. |
| 5,034,099 A | 7/1991 | Nilsson |
| 5,047,332 A | 9/1991 | Chahal |
| 5,052,874 A | 10/1991 | Johanson |
| 5,100,066 A | 3/1992 | Frei |
| 5,114,488 A | 5/1992 | Huber et al. |
| 5,122,228 A | 6/1992 | Bouchette et al. |
| 5,135,861 A | 8/1992 | Pavilon |
| 5,176,295 A | 1/1993 | Stefanik |
| 5,181,804 A | 1/1993 | Wysong et al. |
| 5,188,298 A | 2/1993 | Gerber |
| 5,198,074 A | 3/1993 | Villavicencio et al. |
| 5,221,357 A | 6/1993 | Brink |
| 5,338,366 A | 8/1994 | Grace et al. |
| 5,348,871 A | 9/1994 | Scott et al. |
| 5,366,558 A | 11/1994 | Brink |
| 5,411,594 A | 5/1995 | Brelsford |
| 5,417,492 A | 5/1995 | Christian et al. |
| 5,424,417 A | 6/1995 | Torget et al. |
| 5,487,989 A | 1/1996 | Fowler et al. |
| 5,503,996 A | 4/1996 | Torget et al. |
| 5,504,259 A | 4/1996 | Diebold et al. |
| 5,536,325 A | 7/1996 | Brink |
| 5,571,703 A | 11/1996 | Chieffalo et al. |
| 5,597,714 A | 1/1997 | Farone et al. |
| 5,611,930 A | 3/1997 | Nguyen et al. |
| 5,628,830 A | 5/1997 | Brink |
| 5,677,154 A | 10/1997 | Van Draanen et al. |
| 5,705,213 A | 1/1998 | Guillin |
| 5,705,369 A | 1/1998 | Torget et al. |
| 5,730,837 A | 3/1998 | Black et al. |
| 5,733,758 A | 3/1998 | Nguyen |
| 5,735,916 A | 4/1998 | Lucas et al. |
| 5,791,779 A | 8/1998 | Smith |
| 5,843,760 A | 12/1998 | Zhang et al. |
| 5,863,389 A | 1/1999 | White et al. |
| 5,916,780 A | 6/1999 | Foody et al. |
| 5,932,452 A | 8/1999 | Mustranta et al. |
| 6,022,419 A | 2/2000 | Torget et al. |
| 6,063,204 A * | 5/2000 | Hester et al. ............... 127/1 |
| 6,090,595 A | 7/2000 | Foody et al. |
| 6,199,299 B1 | 3/2001 | Prough et al. |
| 6,228,177 B1 | 5/2001 | Torget |
| 6,330,767 B1 * | 12/2001 | Carr et al. ............... 52/192 |
| 6,336,573 B1 | 1/2002 | Johanson |
| 6,409,841 B1 | 6/2002 | Lombard |
| 6,419,788 B1 | 7/2002 | Wingerson |
| 6,423,145 B1 | 7/2002 | Nguyen et al. |
| 6,498,029 B2 | 12/2002 | Keller, Jr. et al. |
| 6,557,267 B2 | 5/2003 | Wanger |
| 6,569,653 B1 | 5/2003 | Alard et al. |
| 6,572,734 B2 | 6/2003 | Baker |
| 6,620,292 B2 | 9/2003 | Wingerson |
| 6,648,251 B1 | 11/2003 | Chollet |
| 6,660,506 B2 | 12/2003 | Nguyen et al. |
| 6,737,258 B2 | 5/2004 | Hames et al. |
| 6,743,928 B1 | 6/2004 | Zeitsch |
| 6,908,995 B2 | 6/2005 | Blount |
| 6,927,048 B2 | 8/2005 | Verser et al. |
| 7,109,005 B2 | 9/2006 | Eroma et al. |
| 7,178,698 B2 | 2/2007 | Forslund et al. |
| 7,198,925 B2 | 4/2007 | Foody |
| 7,238,242 B2 | 7/2007 | Pinatti et al. |
| 7,396,434 B2 | 7/2008 | Rodriguez Rivera et al. |
| 7,445,691 B2 | 11/2008 | Snekkenes et al. |
| 7,461,591 B2 | 12/2008 | Babbini |
| 7,494,675 B2 | 2/2009 | Abbas et al. |
| 7,503,981 B2 | 3/2009 | Wyman et al. |
| 7,875,444 B2 | 1/2011 | Yang et al. |
| 7,901,511 B2 | 3/2011 | Griffin et al. |
| 7,937,851 B2 | 5/2011 | Rajagopalan et al. |
| 7,993,463 B2 | 8/2011 | Griffin et al. |
| 8,051,986 B2 | 11/2011 | Lees |
| 8,053,566 B2 | 11/2011 | Belanger et al. |
| 8,193,395 B2 | 6/2012 | Fenton et al. |
| 8,449,680 B2 | 5/2013 | Burke et al. |
| 2002/0003032 A1 | 1/2002 | Nay et al. |
| 2002/0164731 A1 | 11/2002 | Eroma et al. |
| 2003/0089465 A1 | 5/2003 | Schaible et al. |
| 2004/0121436 A1 | 6/2004 | Blount |

(56) References Cited

U.S. PATENT DOCUMENTS

| | | |
|---|---|---|
| 2004/0154760 A1 | 8/2004 | Dean |
| 2004/0171136 A1 | 9/2004 | Holtzapple et al. |
| 2004/0231661 A1 | 11/2004 | Griffin et al. |
| 2004/0231811 A1 | 11/2004 | Engstrand et al. |
| 2005/0269048 A1 | 12/2005 | Rodriguez et al. |
| 2006/0088922 A1 | 4/2006 | Yang et al. |
| 2006/0163118 A1 | 7/2006 | Kelsey et al. |
| 2006/0169430 A1 | 8/2006 | Tarasenko |
| 2006/0188965 A1 | 8/2006 | Wyman et al. |
| 2006/0233864 A1 | 10/2006 | Power |
| 2006/0272518 A1 | 12/2006 | Babbini |
| 2006/0275895 A1 | 12/2006 | Jensen et al. |
| 2007/0037267 A1 | 2/2007 | Lewis et al. |
| 2007/0148751 A1 | 6/2007 | Griffin et al. |
| 2007/0209974 A1 | 9/2007 | Lees |
| 2007/0215300 A1 | 9/2007 | Upfal et al. |
| 2007/0218530 A1 | 9/2007 | Duck et al. |
| 2007/0227063 A1 | 10/2007 | Dale et al. |
| 2008/0026431 A1 | 1/2008 | Saito et al. |
| 2008/0038784 A1 | 2/2008 | D'Arnaud-Taylor |
| 2008/0227161 A1 | 9/2008 | Levie et al. |
| 2009/0029432 A1 | 1/2009 | Abbas et al. |
| 2009/0062516 A1 | 3/2009 | Belanger et al. |
| 2009/0069550 A1 | 3/2009 | Belanger et al. |
| 2009/0098616 A1 | 4/2009 | Burke et al. |
| 2009/0098617 A1 | 4/2009 | Burke et al. |
| 2009/0240088 A1 | 9/2009 | Fenton et al. |
| 2009/0246848 A1 | 10/2009 | Noel |
| 2010/0024806 A1 | 2/2010 | Burke et al. |
| 2010/0024807 A1 | 2/2010 | Burke et al. |
| 2010/0024808 A1 | 2/2010 | Burke et al. |
| 2010/0024809 A1 | 2/2010 | Burke et al. |
| 2010/0028089 A1 | 2/2010 | Burke et al. |
| 2010/0124583 A1 | 5/2010 | Medoff |
| 2010/0186736 A1 | 7/2010 | Burke et al. |
| 2011/0011391 A1 | 1/2011 | Burke |
| 2012/0111321 A1 | 5/2012 | Nguyen et al. |

FOREIGN PATENT DOCUMENTS

| | | |
|---|---|---|
| CA | 1147105 A | 5/1983 |
| CA | 1173825 A1 | 9/1984 |
| CA | 1190923 A1 | 7/1985 |
| CA | 1267407 | 3/1990 |
| CA | 1287705 | 8/1991 |
| CA | 2037275 A1 | 8/1992 |
| CA | 1322366 C | 9/1993 |
| CA | 2063547 A1 | 9/1993 |
| CA | 2065939 A1 | 10/1993 |
| CA | 2339002 A1 | 7/1999 |
| CA | 2638150 A1 | 1/2010 |
| CA | 2638159 A1 | 1/2010 |
| CN | 200981760 | 11/2007 |
| EP | 0487793 A1 | 6/1992 |
| EP | 0884391 B1 | 1/2002 |
| EP | 1316620 A2 | 6/2003 |
| EP | 1036236 B1 | 7/2003 |
| FR | 777824 | 3/1935 |
| GB | 892506 | 3/1957 |
| GB | 1043460 A | 9/1966 |
| WO | 9213849 A1 | 8/1992 |
| WO | 9640970 A1 | 12/1996 |
| WO | 9732073 A1 | 9/1997 |
| WO | 0238787 A2 | 5/2002 |
| WO | 2004018645 A2 | 3/2004 |
| WO | 2004081193 A2 | 9/2004 |
| WO | 2004106624 A1 | 12/2004 |
| WO | 2005079190 A2 | 9/2005 |
| WO | 2005118165 A1 | 12/2005 |
| WO | 2006017655 A3 | 2/2006 |
| WO | 2006034591 A1 | 4/2006 |
| WO | 2006055362 A1 | 5/2006 |
| WO | 2006/063467 A1 | 6/2006 |
| WO | 2007009463 A2 | 1/2007 |
| WO | 2007064296 A1 | 6/2007 |
| WO | 2007065241 A1 | 6/2007 |
| WO | 2007111605 A1 | 10/2007 |
| WO | 2008086115 A2 | 7/2008 |
| WO | 2008144903 A1 | 12/2008 |
| WO | 2009012779 A2 | 1/2009 |
| WO | 2009018469 A1 | 2/2009 |
| WO | 2009089439 A1 | 7/2009 |
| WO | 2010006840 A2 | 1/2010 |
| WO | 2010009547 A1 | 1/2010 |
| WO | 2010009548 A1 | 1/2010 |
| WO | 2010009549 A1 | 1/2010 |
| WO | 2010009550 A1 | 1/2010 |
| WO | 2010009551 A1 | 1/2010 |
| WO | 2010083600 A1 | 7/2010 |
| WO | 2010083601 A1 | 7/2010 |
| WO | 2011028554 A1 | 3/2011 |

OTHER PUBLICATIONS

International Search Report received in connection to the co-pending international patent application No. PCT/CA2010/000088, mailed May 14, 2010.

Q.A. Nguyen et al., "NREL/DOE Ethanol Pilot-Plant: Current Status and Capabilities" (1996) 58 Bioresource Technology 189.

R.P. Overend & E. Chornet, "Fractionation of lignocellulosics by steam-aqueous pretreatments" (1987) 321 Phil. Trans. R. Soc. Lond. A. 523.

D. Ballerini et al., "Ethanol Production from Lignocellulosics: Large Scale Experimentation and Economics" (1994) 50 Biousource Technology 17.

K.M.F. Kazi, P. Jollez, & E. Chornet, "Preimpregnation: An Important Step for Biomass Refining Processes" (1998) 15:2 Biomass and Bioenergy 125.

M.P. Tucker et al., "Comparison of Yellow Poplar Pretreatment Between NREL Digester and Sunds Hydrolyzer" (1998) 70-72 Applied Biochemistry and Biotechnology 25.

Charles E. Wyman et al., "Comparative Sugar Recovery Data from Laboratory Scale Application of Leading Pretreatment Technologies to Corn Stover" (2005) 96 Bioresource Technology 2026.

Charles E. Wyman et al., "Coordinated Development of Leading Biomass Pretreatment Technologies" (2005) 96 Bioresource Technology 1959.

Nathan Mosier et al., "Features of Promising Technologies for Pretreatment of Lignocellulosic Biomass" (2005) 96 Biosource Technology 673.

Tim Eggeman & Richard T. Elander, "Process and Economics Analysis of Pretreatment Technologies" (2005) 96 Bioresource Technology 2019.

Abengoa Bioenergy, Press Release, "Abengoa Bionergy Awarded DOE Financial Assistance Agreement" (Feb. 28, 2007), online: Abongoa Bioenergy <http://www.abengoabioenergy.es/corp/web/en/acerca_de/sala_de_prensa/historico/2007/20070228_noticias.html#>.

Outputs from the EPOBIO Workshop, Greece, "Products from Plants—From Crops and Forests to Zero Waste Biorefineries" (May 15-17, 2007).

Abengoa Bioenergy, Press Release, "Abengoa Bionergy Opens Pilot Plant for the Energy of the Future" (Oct. 15, 2007), online: Abengoa Bioenergy <http://www.abengoabioenergy.es/corp/web/en/acerca_de/sala_de_prensa/historico/2007/20071015_noticias.html#>.

Merrick & Company, Final Report of Jun. 14, 1999, "Softwood Biomass to Ethanol Feasibility Study" (Aug. 2004) Subcontractor Report published by National Renewable Energy Laboratory.

Merrick & Company, Final Report of Jan. 2000, Building a Bridge to the Corn Ethanol Industry. Corn Stover to Ethanol at High Plains Corporation's York, Nebraska Co-Located Plant Site.

Melvin P. Tucker et al., "Conversion of Distiller's Grain into Fuel Alcohol and a Higher-Value Animal Feed by Dilute-Acid Pretreament" (2004) 113-116 Applied Biochemistry and Biotechnology 1139.

Melvin P. Tucker et al., "Effects of Temperature and Moisture on Dilute-Acid Steam Explosion Pretreatment of Corn Stover and Cellulase Enzyme Digestibility" (2003) 105-108 Applied Biochemistry and Biotechnology 165.

(56) References Cited

OTHER PUBLICATIONS

Kyoung Heon Kim et al., "Continuous Countercurrent Extraction of Hemicellulose from Pretreated Wood Residues" (2001) 91-93 Applied Biochemistry and Biotechnology 253.
Quang A. Nguyen et al., "Two-Stage Diute-Acid Pretreatment of Softwoods" (2000) 84-86 Applied Biochemistry and Biotechnology 561.
Daniel J. Schell et al., "Dilute-Sulfuric Acid Pretreatment of Corn Stover in Pilot-Scale Reactor" (2003) 105-108 Applied Biochemistry and Biotechnology 69.
Q.A. Nguyen & J.N. Saddler, "An Integrated Model for the Technical and Economic Evaluation of an Enzymatic Biomass Conversion Process" (1991) 35 Bioresource and Technology 275.
Q.A. Nguyen et al., "Dilute Acid Pretreatment of Softwoods", Scientific Note, (1998) 70-72 Applied Biochemistry and Biotechnology 77.
Q.A. Nguyen et al., "Dilute Acid Hydrolysis of Softwoods", Scientific Note, (1999) 77-79 Applied Biochemistry and Biotechnology 133.
Raphael Katzen & Donald F. Othmer, "Wood Hydrolysis. A Continuous Process" (1942) 34 Industrial and Engineering Chemistry 314.
"Transactions of the Institution of Chemical Engineers" (1993) 11 Institution of Chemical Engineers, London, the United Kingdom.
Diane Knappert, Hans Grethlein & Alvin Converse, "Partial Acid Hydrolysis of Cellulosic Materials as a Pretreatment for Enzymatic Hydrolysis" (1980) 22 Biotechnology and Bioengineering 1449.
Sung Bae Kim & Y.Y. Lee, "Diffusion of Sulfuric Acid within Lignocellulosic Biomass Particles and its Impact on Dilute-Acid Pretreatment" (2002) 83 Bioresource Technology 165.
Alan W. Roberts, "Design Considerations and Performance Evaluation of Screw Conveyors", online: The South African Institute of Materials Handling <http://www.saimh.co.za/beltcon/beltcon11/beltcon1114.htm>.
National Renewable Energy Laboratory, "Process Design and Cost Estimate of Critical Equipment in the Biomass to Ethanol Process. Acid Hydrolysis Reactors Batch Systems", Report (Seattle, Washington: Harris Group Inc., 2001).
Osamu Kitani & Carl W.. Hall, eds., "Biomass Handbook" 470-474 (Gordon and Breach Science Publishers: New York).
Buell Classifier Fisher-Klosterman, Leaflet, "Operation Principles and Efficiency".
Process Sensors Corporation, "On-Line Moisture Measurement and Control Manufacturing Industries Worldwide", Product Information, online: Process Sensors Corporation <http://processsensors.com/index.html?gclid=CKT27fXvJ0CFREWagodclkUcw>.
Roger M. Rowell, Raymond A. Young, & Judith K. Rowell, eds., Paper and Composites from Agro-Based Resources (Lewis Publishers).
G.H.Emert et al., "Gasohol/Biomass Developments: Economic Update of the Gulf Cellulose Alcohol Process" (Sep. 1980) Chemical Engineering Progress 47.
Ron Kotrba, "The Project of a Lifetime" (Feb. 2006), Ethanol Producer Magazine.
National Renewable Energy Laboratory, "Research Advances: NREL Leads the Way. Cellulosic Ethanol", Brochure, (Mar. 2007), online: National Renewable Energy Laboratory <http://www.nrel.gov/biomass/pdfs/40742.pdf>.
National Renewable Energy Laboratory, Fact Sheet, "Clean Cities: Ethanol Basics" (Oct. 2008), online: U.S. Department of Energy <www.ardc.energy.gov/afdc/pdfs/43835.pdf>.
Brent D. Yacobucci, "Fuel Ethanol: Background and Public Policy Issues", (Mar. 3, 2006), CRS Report for Congress, online: U.S. Department of State, Foreign Press Centre <fpc.state.gov/documents/organization/62837.pdf>.
U.S. Department of Energy, Energy Efficiency & Renewable Energy, Alternative Fuels & Advanced Vehicles Data Center, Article, "Ethanol Market Penetration", online: U.S Department of Energy <http://www.afdc.energy.gov/afdc/ethanol/market.html>.
Kenneth W.Britt, ed., "Handbook of Pulp and Paper Technology", 2nd. ed. (New York: Van Nostrand Reinhold Company).

A. Aden et al., "Lignocellulosic Biomass to Ethanol Process Design and Economics Utilizing Co-Current Dilute Acid Prehydrolysis and Enzymatic Hydrolysis for Corn Stover", (Jun. 2002), Technical Report published by National Renewable Energy Laboratory.
U.S. Department of Energy Office of Science, Genomics Science Program, "Fuel Ethanol Production", online: U.S. Department of Energy Office of Science <http://genomicscience.energy.gov/biofuels/ethanolproduction.shtml>.
Metso Automation, Metso Automation's Newsletter for Neles and Jamesbury products, "Biofuels—a growth market for Metso", (Summer 2008), online: Metso <http://valveproducts.metso.com/metsoautomation/DocDB/catalogs/catalog.taf?pg_parent=397>.
SunOpta Inc., News Release, "SunOpta Announces Sale of Cellulosic Ethanol Facility to China Resources Alcohol Corporation", (Jun. 23, 2006), online: SunOpta Inc. <http://investor.sunopta.com/releasedetail.cfm?ReleaseID=287111>.
Ralph P. Overend, Slideshow, "The Lignocellulosic bottleneck: material properties, architecture and pretreatment".
Robert Wooley et al., "Lignocellulosic Biomass to Ethanol Process Design and Economics Utilizing Co-Current Dilute Acid Prehydrolysis and Enzymatic Hydrolysis Current and Futuristic Scenarios", (Jul. 1999), National Renewable Energy Laborator. Technical Report.
Nathan S. Masier, "Cellulosic Ethanol—Biofuel Beyond Corn" Bio Energy, Purdue University.
U.S Securities and Exchange Commission, "Annual Report Under Section 13 or 15(d) of the Securities Exchange Act of 1934", for Bluefire Ethanol Fuels, Inc. Signed on Feb. 28, 2008.
U.S Securities and Exchange Commission, "Annual Report Under Section 1 or (15)d of the Securities Exchange Act of 1934", for CleanTech Biofuels, Inc. Signed on Mar. 28, 2008.
*Abengoa Bioenergy New Technologies Inc. f/k/a Abengoa Bioenergy R&D, Inc.* v. *Mascoma Corporation*; Notice of Arbitration and Statement of Claim, submitted to American Arbitration Association Commercial Arbitration Tribunal on Nov. 2, 2011.
"Easy Steps for Optimal Yeast Rehydration," Laboratory Protocol, Scott Laboratories, Petaluma CA, 1 page.
"Enzyme Sugar-Ethanol Platform Project," NREL, U.S. Dept. of Energy by Midwest Research Institute, Battelle, Bechtel, 47 pages.
"Ethanol Annual Report FY 1990", SERI, TP-231/3996, Prepared for the U.S. DOE, Jan. 1991, Contract No. DE-AC02-83CH10093, Texeira, R.H. and Goodman, B.J., editors, 344 pages.
"Lessons Learned from Existing Biomass Power Plants," Feb. 2000, NREL/SR-570-26946, G. Wiltsee, Appel Consultants, Inc., Valencia, CA, 149 pages.
"Process Design and Cost Estimate of Critical Equipment in the Biomass to Ethanol Process, Report 99-10600/17 Continuous Acid Hydrolysis Reactor," Jan. 22, 2011 Rev WEB, Subcontract ACO-9-29067-01, National Renewable Energy Laboratory, Golden, CO, Harris Group Inc., Seattle, WA, 14 pages.
"Types of Lignin and Their Properties," 2001, Information Service from the Lignin Institute, 9/1:4 pages, www.lignin.org/01augdialogue.html.
Abstract of Chinese Patent Application CN 101310879 A, 2008, Institute of Process Engineering, Chinese Academy of Sciences.
Activator 90, Product Brochure, 2009, Loveland Products Inc., No. 6566_05/09, 1 page.
Al-Halaly, A.S.M., "A Study of Some Anatomical Chemical Properties and Specific Gravity of Casuarina Equisetifolia Forst. Wood Grown in Iraq," 1985, AGRIS Record No. IQ8500239, Abstract, 1 page.
Amistco Tower Trays, Product Brochure, Amistco Separation Products, Inc., 8 pages.
Antongiovanni, M., et al., "Variability in Chemical Composition of Straws," 1991, CIHEAM—Options Mediterraneennes, Serie Seminaires, 16:49-53.
Dowe, N., et al., "SSF Experimental Protocols-Lignocellulosic Biomass Hydrolysis and Fermentation, Laboratory Analytical Procedure (LAP)," Jan. 2008, NREL Technical Report, NREL/TP-510-42630, 19 pages.
Duff, S.J.B. et al., "Bioconversion of Forest Products Industry Waste Cellulosics to Fuel Ethanol: A Review", 1996, Bioresource Technology, 55:1-33.

(56) References Cited

OTHER PUBLICATIONS

Esteghlalian, A., et al., "Modeling and Optimization of the Dilute-Sulfuric-Acid Pretreatment of Corn Stover, Poplar and Switchgrass," 1997, Bioresource Technology, 59:129-136.
Fan, L.T., et al., "Evaluation of Pretreatments for Enzymatic Conversion of Agricultural Residues," 1981, Biotechnology & Bioengineering Symposium, 11:29-45 (Proceedings of the Third Symposium on Biotechnology in Energy Production and Conservation, Gatlinburg, TN, May 12-15, 1981).
Flexitray Valve Trays, Product Brochure, Koch-Glitsch, Bulletin FTCVT-01, Revised Mar. 2010, 12 pages.
Flint, S.I., et al., "Recovery of Lignin During Nonstarch Polysaccharide Analysis," 1992, Cereal Chem, 69/4:444-447.
Foody, P., "Optimization of Steam Explosion Pretreatment," 1980, Final Report to DOE, Report No. DOE/ET23050-1, Contract No. AC02-79ET23050, Bibliographic Citation, 1 page.
Fuel Ethanol Application Sheet, "CELLIC Ctec and Htec2—Enzymes for Hydrolysis of Lignocellulosic Materials," Novozymes A/S, Luna No. 2010-01668-01, 9 pages.
Gea Wiegand, GmbH, Process Engineering Division, "Bioethanol Technology", Ettlingen, Germany, Company Brochure, 16 pages.
Gea Wiegand, GmbH, Process Engineering Division, "Distillation Technology", Ettlingen, Germany, Company Brochure, 16 pages.
Ghose, T.K., "Measurement of Cellulase Activities," 1987, Pure and Appl. Chem., 59/2:257-268.
PCT International Search Report, dated Oct. 8, 2010, corresponding to International application No. PCT/CA2010/001091.
Juhasz, T., et al., "Characterization of Cellulases and Hemicellulases Produced by *Trichoderma reesei* on Various Carbon Sources," 2005, Process Biochem, 40:3519-3525.
Keller, F.A., et al., "Yeast Adaptation on Softwood Prehydrolysate," 1998, Appl Biochem and Biotech, 70-72:137-148.
Kolar, L, et al., "Agrochemical Value of Organic Matter of Fermenter Wastes in Biogas Production," 2008, Plant Soil Environ, 54/8:321-328.
Kumar, R., et al., "The Impact of Dilute Sulfuric Acid on the Selectivity of Xylooligomer Depolymerization to Monomers," 2008, Carbohydrate Res, 343:290-300.
Linde, M., et al., "Steam Pretreatment of Acid-Sprayed and Acid-Soaked Barley Straw for Production of Ethanol," 2006, Appl Biochem and Biotech, 129-132:546-562.
Liu, H., et al., "Lignin-Metal Complexation to Eliminate Nonproductive Enzyme Adsorption by Lignin in Unwashed Lignocellulosic Substrates," 2010, 32nd Symposium on Biotechnology for Fuels and Chemicals, 28 pages.
Office action issued in Canadian Application No. 2,638,152, dated Feb. 8, 2011, 4 pages.
Ohgren, K., et al., "High Temperature Enzymatic Prehydrolysis Prior to Simultaneous Saccharification and Fermentation of Steam Pretreated Corn Stover for Ethanol Production," 2007, Enzyme Microb Technol, 40/4:607-613.
Pan, X., et al., "Bioconversion of Hybrid Poplar to Ethanol and Co-Products Using an Organosolv Fractionation Process: Optimization of Process Yields," 2006, Biotech and Bioeng, 94/5:851-861.
PROPAX Yeast Propagation Technology, Product Brochure, Meura S.A., Edited 2009, 2 pages.
Ramsay, J.A., et al., "Biological Conversion of Hemicellulose to Propionic Acid," 1998, Enzyme Microb Technol, 22:292-295.
Schell, D.J., et al., "A Bioethanol Process Development Unit: Initial Operating Experiences and Results with a Corn Fiber Feedstock," 2004, Bioresource Technology, 91:179-188.
Sharma-Shivappa, R.R., et al, "Conversion of Cotton Wastes to Bioenergy and Value-Added Products," 2008, Transactions of the ASABE, 51/6:2239-2246.
SILWET L-77 Surfactant, Specimen Label, Helena Chemical Company, Copyright 2006, 2 pages.
Sluiter, A., et al., "Determination of Ash in Biomass, Laboratory Analytical Procedure (LAP)," NREL Technical Report, NREL/TP-510-42622, Jan. 2008, 8 pages.
Sluiter, A., et al., "Determination of Extractives in Biomass, Laboratory Analytical Procedure (LAP)," NREL Technical Report, NREL/TP-510-42619, Jan. 2008, 12 pages.
Sluiter, A., et al., "Determination of Structural Carbohydrates and Lignin in Biomass, Laboratory Analytical Procedure (LAP)," NREL Technical Report, NREL/TP-510-42618, Apr. 2008, 16 pages.
Sluiter, A., et al., "Determination of Sugars, Byproducts, and Degradation Products in Liquid Fraction Process Samples, Laboratory Analytical Procedure (LAP)," NREL Technical Report, NREL/TP-510-42623, Jan. 2008, 14 pages.
Sluiter, A., et al., "Determination of Total Solids in Biomass and Total Dissolved Solids in Liquid Process Samples, Laboratory Analytical Procedure (LAP)," NREL Technical Report, NREL/TP-510-42621, Mar. 2008, 9 pages.
Sun, L., "Silicon-Based Materials from Rice Husks and Their Applications," 2001, Ind Eng Chem Res, 40/25:5861-5877, Abstract Only, 1 page.
Superfrac High Performance Trays, Product Brochure, Koch-Glitsch, Bulletin KGSF-1, Revised Mar. 2010, 16 pages.
Taherzadeh, M. J. et al., "Pretreatment of Lignocellulosic Wastes to Improve Ethanol and Biogas Production: A Review," 2008, Int. J. Mol. Sci., (9) 1621-1651.
Teleman, et al., "Progress-Curve Analysis Shows that Glucose Inhibits the Cellotriose Hydrosysis Catalysed by Cellobiohydrolase II from *Trichoderma reesi*," 1995, European J Biochem, 231:250-258.
The Artisan Dualflo Tray, Product Brochure, Artisan Industries, Inc., Bulletin 9801, Edit Date Apr. 17, 2003, 2 pages.
Thomas, S., et al., "Biofuels Program C-Milestone Completion Report," FY02, DOE Biofuels Program, Report #373, 2002, 51 pages.
Thomas, S.R., "Corn Stover Feedstock Variability," 2005, Feedstock Area Stage Gate Review Meeting, 34 pages.
Thompson, D.N., et al., "Post-Harvest Processing Methods for Reduction of Silica and Alkali Metals in Wheat Straw," 2002, 24th Symposium on Biotechnology for Fuels and Chemicals, Poster #1-30, 21 pages.
Viamajala, S., et al., "Catalyst Transport in Corn Stover Internodes," 2005, Appl Biochem and Biotech, 129-132:509-527.
Weiss, N.D., et al., "Catalyst Impregnation for High Solids Biomass Pretreatment," 2008, AIChE Annual Meeting, 24 pages.
Yang, B., et al., "Chapter 6. Unconventional Relationships for Hemicellulose Hydrolysis and Subsequent Cellulose Digestion," 2004, Lignocellulose Biodegradation, ACS Symposium Series 889, American Chemical Society, pp. 100-125.
"Biofuels Pilot Plant Under Way," Newsbriefs, Chemical Week, Oct. 13/20, 2008, p. 4.
Awafo, V.A., et al., "Evaluation of Combination Treatments of Sodium Hydroxide and Steam Explosion for the Production of Cellulase-Systems by Two *T. reesei* Mutants Under Solid-State Fermentation Conditions," 2000, Bioresource Tech, 73:235-245.
Azadbakht, M., et al., "Preparation of Lignin From Wood Dust as Vanillin Source and Comparison of Different Extraction Methods," Oct. 2004, Int J of Biol and Biotech, 1/4:535-537, Abstract Only, 1 page.
Bakker, R. R., et al., "Biofuel Production from Acid-Impregnated Willow and Switchgrass," 2nd World Conference on Biomass for Energy, Industry and Climate Protection, May 10-14, 2004, Rome, Italy, pp. 1467-1470.
Bigelow, M., et al., "Cellulase Production on Bagasse Pretreated with Hot Water," 2002, App Biochem and Biotech, 98-100:921-934.
Brownell, H.H., et al., "Steam-Explosion Pretreatment of Wood: Effect of Chip Size, Acid, Moisture Content and Pressure Drop," 1986, Biotechnol Bioeng, 28/6:792-801, Abstract Only, 1 page.
Coons, R., "DSM Launches Cellulosic Biofuel Project," Oct. 27, 2008, Chemical Week, 170/33:9.
Coons, R., "Novozymes Ramps Up Focus on Second-Generation Biofuels," Oct. 27, 2008, Chemical Week, 170/33:30.
Cullis, I.F., et al., "Effect of Initial Moisture Content and Chip Size on the Bioconversion Efficiency of Softwood Lignocellulosics," 2004, Biotechnol Bioeng, 85/4:413-421, Abstract Only, 1 page.
Cunningham, R.L., et al., "Improved Hemicellulose Recovery From Wheat Straw," 1985, Biotech and Bioeng Symp No. 15, Seventh Symposium on Biotechnology for Fuels and Chemicals, pp. 17-26.

(56) References Cited

OTHER PUBLICATIONS

Dasari, R.K., et al., "The Effect of Particle Size on Hydrolysis Reaction Rates and Rheological Properties in Cellulosic Slurries," 2007, Appl Biochem and Biotech, Session 2, 137-140/1-2, 289-299, Abstract Only.

De Castro, F.B., "The Use of Steam Treatment to Upgrade Lignocellulosic Materials for Animal Feed," 1994, Thesis, University of Aberdeen, 214 pages.

Grethlein, H.E., "Chemical Breakdown of Cellulosic Materials," 1978, J. Appl. Chem. Biotechnol. 28:296-308.

Grethlein, H.E., et al., "Common Aspects of Acid Prehydrolysis and Steam Explosion for Pretreating Wood," 1991, Bioresource Technology, 36:77-82.

Grohmann, K, et al., "Optimization of Dilute Acid Pretreatment of Biomass," Proceedings of the Seventh Symposium on Biotechnology for Fuels and Chemicals, May 14-17, 1986, 24 pages.

Hames, B., et al., "Determination of Protein Content in Biomass, Laboratory Analytical Procedure (LAP)," May 2008, NREL Technical Report, NREL/TP-510-42625, 8 pages.

Hames, B., et al., "Preparation of Samples for Compositional Analysis, Laboratory Analytical Procedure (LAP)," Aug. 2008, NREL Technical Report, NREL/TP-510-42620, 12 pages.

International Search Report and the Written Opinion issued in connection with PCT Application No. PCT/CA2009/001032, mailed on Oct. 27, 2009, 11 pages.

International Search Report and the Written Opinion issued in connection with PCT Application No. PCT/CA2009/001035, dated Nov. 5, 2009, 7 pages.

International Search Report and the Written Opinion issued in connection with PCT Application No. PCT/CA2009/001036, dated Nov. 13, 2009, 6 pages.

International Search Report issued in connection with PCT Application No. PCT/CA2010/000088, mailed as a corrected version on Jun. 17, 2010.

International Search Report and the Written Opinion issued in connection with international application No. PCT/CA2009/001033, mailed on Oct. 30, 2009.

International Search Report and the Written Opinion issued in connection with PCT Application No. PCT/US2010/46561, dated Dec. 20, 2010, 16 pages.

International Search Report and the Written Opinion issued in PCT Application No. PCT/CA2009/001034, dated Oct. 20, 2009, 9 pages.

International Preliminary Report of Patentability issued in connection with International Application No. PCT/CA2009/001034, issued on Jan. 25, 2011.

International Search Report and the Written Opinion issued in PCT Application No. PCT/US2012/022552, dated May 15, 2012, 18 pages.

Written Opinion of the International Searching Authority, dated Oct. 8, 2010, corresponding to International application No. PCT/CA2010/001091.

Zimbardi, F., et al., "Acid Impregnation and Steam Explosion of Corn Stover in Batch Processes," 2007, Ind Crops and Products, 26:195-206.

"Enzyme Sugar-Ethanol Platform Project," NREL, U.S. Dept. of Energy by Midwest Research Institute, Battelle, Bechtel, 2002, 47 pages.

\* cited by examiner

METHOD AND APPARATUS FOR CONVEYING A CELLULOSIC FEEDSTOCK

FIELD

The invention relates to a method and apparatus for obtaining and conveying a cellulosic feedstock, which may be used for the subsequent production of a fermentable sugar stream from the cellulose and hemicellulose in the cellulosic feedstock wherein the fermentable sugar stream may be used for subsequent ethanol production. More specifically, the invention relates to a method and apparatus for withdrawing one or more feedstock streams from a holding tank.

BACKGROUND

Several processes for the production of ethanol are known. Generally, the production of fuel ethanol involves the fermentation of sugars with yeast. Typically, the sugars are derived from grains, such as corn and wheat. The starches in the grains are subjected to enzymatic hydrolysis in order to produce the sugars, which are then subjected to fermentation to produce ethanol.

Plant materials are a significant source of fermentable sugars, such as glucose, that can be transformed into biofuels. However, the sugars in plant materials are contained in long polymeric chains of cellulose and hemicellulose. Utilizing current fermentation processes, it is necessary to break down these polymeric chains into monomeric sugars, prior to the fermenting step.

Recently, processes have been developed for utilizing cellulosic feedstock, such as corncobs, straw, and sawdust, to produce sugars for ethanol fermentation. Such processes typically comprise pre-treating the feedstock to increase the accessibility of the cellulose to hydrolysis enzymes, and subjecting the cellulose to cellulase enzyme systems to convert the cellulose into glucose.

Methods of converting plant biomass into fermentable sugars are known in the art and in general comprise two main steps: a pre-treatment step to activate the plant structure, and an enzymatic or chemical hydrolysis step to convert the polymeric chains of cellulose and hemicellulose into monomeric sugars. Several approaches have been used for the pre-treatment step, e.g., autohydrolysis, acid hydrolysis, ammonia activation, kraft pulping, organic solvent pulping, hot water pre-treatment, ammonia percolation, lime pre-treatment, caustic soda pulping, or alkali peroxide pre-treatment. Early pre-treatment steps included grinding or milling the feedstock into a powder, which was then mixed with water to form a slurry.

More recently, solvent based pre-treatments, alkali pre-treatments, and acidic pre-treatments have also been described. PCT publication WO/2007/009463 to Holm Christensen describes an alternate pre-treatment, which does not involve the addition of acids, bases, or other chemicals. This pre-treatment process involves soaking the cellulosic material in water, conveying the cellulosic material through a heated and pressurized reactor, and pressing the cellulosic material to produce a fiber fraction and a liquid fraction. After pressing the cellulosic material, the cellulosic material is exposed to hydrolysis enzymes.

Each pre-treatment technology has a different mechanism of action on the plant structure, inducing either physical and/or chemical modifications. However, the main objective of the pre-treatment is to provide accessibility of the plant material to the enzymes.

SUMMARY

The commercial viability of a hydrolysis process is dependent on the character of the feedstock provided to the hydrolysis unit. Typically, this requires that a feedstock is activated such that a significant portion (e.g., greater than 75%) of the cellulose and hemicellulose of the feedstock is accessible to hydrolysis enzymes. If such an activated feedstock is provided to an enzymatic hydrolysis unit, then at least 60%, preferably more than 75% and more preferably over 90% of the cellulose and hemicelluloses may be converted to monomeric sugars. This sugar rich process stream may subsequently be subjected to fermentation to produce an alcohol stream. The alcohol stream from the fermentation stage (i.e., the raw alcohol stream) may have an ethanol content of about 3-22% v/v, preferably about 5-15% and more preferably more about 8-12%.

An activated feedstock for enzymatic hydrolysis is preferably prepared by autohydrolysis, which is preferably conducted in a steam explosion reactor also known as a hydrolyzer (also known as a digester). Autohydrolysis is a process of breaking down hemicellulose and cellulose by exposure to high temperatures, steam and pressure, sometimes in the presence of an added chemical agent, such as an organic or inorganic acid, e.g., sulphuric acid. When performed in the presence of an added acid, the reaction is known as an acid hydrolysis.

During autohydrolysis, the degree of polymerization of cellulose and hemicellulose may be reduced from about 10,000 to about 1,500-1,000. This process is preferably carried out above the glass transition temperature of lignin (120-160° C.). Depending upon the severity of the reaction, degradation products may be produced, such as furfural, hydroxyl-methylfurfural, formic acid, levulinic acid and other organic compounds.

During a steam explosion treatment (more commonly called autohydrolysis if no externally added catalyst), a cellulosic feedstock is subjected to elevated heat (e.g., 180° C. to 220° C.) and pressure (e.g., 130 psig to 322 psig) optionally in the presence of suitable chemicals (e.g., organic and/or inorganic acids, ammonia, caustic soda, sulfur dioxide, solvents etc.) in a pressurized vessel. Preferably, external chemical addition is not utilized; in which case, the only catalyst that may be present may be acetic acid that is generated in situ. The treated cellulosic feedstock is then released from the pressurized vessel such that the pressure is rapidly reduced (e.g., 1 second or less). The biomass may exit the hydrolyzer into a reduced pressure, preferably atmospheric pressure and, more preferably into a vacuum. The rapid decrease in pressure results in the biomass separating into individual fibers or bundles of fiber. This step opens the fiber structure and increases the surface area. The lignin remains in the fiber along with cellulose and residual hemicellulose. Accordingly, the explosive release of pressure, combined with the high temperature and pressure treatment results in the physicochemical modification of the cellulosic feedstock that is then suitable for feeding to an enzymatic hydrolysis unit.

In order for the steam explosion process to be able to produce an activated feedstock that is capable of producing such a sugar rich process stream, the temperature and moisture level of the cellulosic feedstock that is fed to a steam explosion reactor preferably is relatively uniform and preferably has a temperature from about 50 to about 70° C., and more preferably 50-65° C. and a moisture content from about 30 to about 60 wt % (preferably 45 to about 55 wt %). Moisture content is the quantity of water contained in a material, and on a weight basis, is the weight of water in the material divided by the mass of the material.

It is preferred that the fiber in the feedstock fed to an autohydrolysis unit have a relatively uniform temperature profile. For example, it is preferred that the core of the blocks of material have a temperature that is within 80%, more preferably 90%, most preferably 95% of the temperature of the exterior surface of the material. Accordingly, for example, if the temperature of the exterior surface of the material is from 50 to 70° C., then the temperature of the core of the material is preferably from 45 to 63° C.

Alternately, or in addition, it is preferred that the fiber in the feedstock fed to an autohydrolysis unit have a relatively uniform moisture profile. For example, it is preferred that the core of the blocks of material have a moisture content that is within 80%, more preferably 90%, most preferably 95% of the moisture content of the exterior surface of the material. Accordingly, for example, if the moisture content of the exterior surface of the material is from 45 to 55 wt %, then the moisture content of the core of the material is preferably from 40.5 to 49.5 wt %.

Embodiments of the present invention provide a method and apparatus for preparing a cellulosic feedstock for ethanol production. The method and apparatus relate to an apparatus, such as a holding tank, that may be positioned downstream from a cellulosic feedstock pre-treatment process, such as a mixing vessel that impregnates the cellulosic feedstock with heat and moisture, and upstream from hydrolysis reactors, such as an autohydrolysis reactor.

Further, embodiments in accordance with this invention may be advantageous because obtaining two streams and feeding the two streams into different hydrolysis reactors allows for the hydrolysis reactors to be operated on a batch basis and to be operated such that at least one hydrolysis reactor is out of phase with another hydrolysis reactor. That is, a first hydrolysis reactor may be filled from a first stream while a second hydrolysis reactor is operated to hydrolyze a cellulosic feedstock obtained from a second stream. Accordingly, the overall process may be a continuous process, while the hydroysis process may be operated on a batch process.

As the material is transported to one or more process units (e.g., hydrolysis units) wherein the feedstock will be broken down, such as in the preparation of a fermentable sugar stream, the material preferably travels downward through a vessel or conduit from which it must then be withdrawn. For example, the material may be passed through a hopper, a holding tank with a bottom outlet, a process vessel with a bottom outlet or the like and, preferably a holding tank. As the material is preferably substantially a solid, it does not flow freely. Therefore, while the material may travel downwardly under the influence of gravity, not all portions will travel downwardly at the same rate. The portions closer to the wall of a vessel may have a tendency to stick to the sidewall or travel downwardly slower due to friction between the sidewall and the material adjacent the sidewall. This may result in different residence times for some portions of the feedstock. If the sidewall is heated (e.g. surrounded by a heating jacket), portions of the material closer to the sidewall may overheat if the residence time is too long, causing sugar in the feedstock to degrade. Accordingly, it is preferred that the feedstock is actively withdrawn from such equipment to obtain the multiple process streams.

In accordance with one aspect of the instant invention, there is provided a method of preparing a cellulosic feedstock for ethanol production, comprising:

(a) passing the cellulosic feedstock through a vessel to at least one outlet of the vessel;

(b) passing the cellulosic feedstock out of the at least one outlet of the vessel and obtaining at least two streams of cellulosic feedstock; and, (c) feeding the at least two streams to different hydrolysis reactors.

In any embodiment, step (b) may comprise conveying the cellulosic feedstock laterally across the outlet of the vessel, preferably in different directions.

In any embodiment, the method may further comprise operating the different hydrolysis reactors on a batch basis and operating at least one hydrolysis reactor out of phase with another hydrolysis reactor. Preferably, a first hydrolysis reactor is filled from a first stream while a second hydrolysis reactor is operated to hydrolyze cellulosic feedstock obtained from a second stream.

In any embodiment, the method may further comprise passing the cellulosic feedstock downwardly through the vessel.

In any embodiment, the vessel may comprise at least four conveying devices proximate the at least one outlet of the vessel, and step (b) may comprise utilizing at least two conveying devices to convey a first portion of the cellulosic feedstock in a first direction to obtain the first stream, and utilizing at least two conveying devices to convey a second portion of the cellulosic feedstock in a second direction to obtain the second stream. Preferably, a first portion of cellulosic feedstock for the first stream is drawn from a first portion of the outlet and a second portion of cellulosic feedstock for the second stream is drawn from a second portion of the outlet. For example, the first portion may comprise one side of the outlet and the second portion may comprise a second side of the outlet (e.g., the outlet may be essentially divided in half with each side comprising a portion). In such a case, two conveying devices that operate to withdrawn the feedstock to form a first steam may be positioned under one side and two conveying devices that operate to withdrawn the feedstock to form a second steam may be positioned under the other side.

In any embodiment, the at least one inlet of the vessel is preferably disposed at an elevation above the at least one outlet of the vessel, and the cellulosic feedstock is preferably conveyed from the at least one inlet towards the at least one outlet of the vessel under the force of gravity.

In any embodiment, the residence time of the cellulosic in the vessel is preferably up to 60 minutes, and, more preferably between 10 minutes and 30 minutes.

In any embodiment, the method may further comprise applying heat to the cellulosic feedstock in the vessel.

In any embodiment, steps (a) to (c) are preferably performed on a continuous basis.

It will be appreciated that, in any embodiment, the cellulosic feedstock conveyed through the vessel is a solid and may be of any composition disclosed herein.

In accordance with another aspect of the instant invention, there is also provided an apparatus for use in preparing a cellulosic feedstock for ethanol production, comprising:

(a) at least one sidewall defining a volume having an upper portion and a lower portion;

(b) at least one inlet adjacent the upper portion;

(c) at least one outlet adjacent the lower portion;

(d) at least a first conveyor proximate the at least one outlet configured to convey a first portion of the cellulosic feedstock laterally across the at least one outlet in a first direction; and, (e) at least a second conveyor proximate the at least one outlet configured to convey a second portion of the cellulosic feedstock laterally across the at least one outlet in a second direction.

In any embodiment, the first and second conveyors are preferably positioned adjacent each other.

In any embodiment, the first conveyor preferably conveys cellulosic feedstock towards an outlet of the first conveyor, and the second conveyor preferably conveys cellulosic feedstock towards an outlet of the second conveyor.

In any embodiment, the first direction is preferably generally opposite to the second direction.

In any embodiment, all of the outlet is preferably exposed to the conveyors.

In any embodiment, the conveyors may be provided in a housing having at least one conveyor outlet in a lower surface thereof for each conveyor.

In any embodiment, each conveyor may comprise at least one rotatably mounted helical screw, and preferably at least two helical screws that are rotatable in the same direction. Alternately, or in addition, in any embodiment, one or more, and preferably each conveyor comprises at least one rotatably mounted helical screw having a variable pitch.

In any embodiment, the apparatus may further comprise a housing for the conveyors and a heating jacket disposed at least partially around the housing.

It will be appreciated that each of the embodiments may be used by itself in the method or aspect provided in accordance with this invention. It will further be appreciated that each of the embodiments may be used with any other embodiments or embodiments such that the embodiments may be used individually or all together in combination or in any sub-combination.

BRIEF DESCRIPTION OF THE DRAWINGS

These and other advantages of the present invention will be more fully and particularly understood in connection with the following description of the preferred embodiments of the invention in which.

DETAILED DESCRIPTION OF THE INVENTION

An embodiment of an apparatus of the present invention is shown in FIGS. 1-10. It will be appreciated that although the method is described with reference to the apparatus and vice versa, the method may be carried out with an alternate apparatus, and the apparatus may be used according to an alternate method. Furthermore, although the production of the cellulosic feedstock that is provided to the vessel in accordance with this invention is described as a continuous process, it will be appreciated that the method may be carried out as a semi-continuous or batch process.

The cellulosic feedstock is preferably a lignocellulosic feedstock. A lignocellulosic feedstock is derived from plant materials. As used herein, a "lignocellulosic feedstock" refers to plant fiber containing cellulose, hemicellulose and lignin. In some embodiments, the feedstock may be derived from trees, preferably deciduous trees such as poplar (e.g., wood chips). Alternately or in addition, the feedstock may also be derived from agricultural residues such as, but not limited to, corn stover, wheat straw, barley straw, rice straw, switchgrass, sorghum, bagasse, rice hulls and/or corn cobs. Preferably, the lignocellulosic feedstock comprises agricultural residues and wood biomass, more preferably wood biomass and most preferably deciduous. The applicants contemplate other sources of plant materials comprising cellulose, hemicellulose and/or lignin, such as algae, for use in deriving cellulosic feedstocks and any of those may be used.

The cellulosic feedstock is preferably cleaned, e.g., to remove ash, silica, metal strapping (e.g., from agricultural products), stones and dirt. The size of the components of the lignocellulosic feedstock may also be reduced. The size of the components of the feedstock may be from about 0.05 to about 2 inches, preferably from about 0.1 to about 1 inch, and more preferably from about 0.125 to about 0.5 inches in length. For example, the cellulosic feedstock may comprise fibers, e.g., chopped straw, of a length of between about 4 mm (0.16 inches) and about 7 mm (0.28 inches). Any process machinery that is able to crush, grind or otherwise decrease the particle size may be utilized.

The feedstock is preferably treated with water so as to have a moisture content upon entry to the vessel (e.g., holding tank 100) of between about 30 and about 60 preferably between about 45 and about 55 wt %. For example, referring to FIGS. 1 and 2, an embodiment of a holding tank apparatus 100 of the present invention is shown wherein the holding tank 100 is positioned downstream from a water impregnation reactor such as impregnation chamber 10, which is preferably used to pre-treat the feedstock prior to the feedstock entering holding tank 100. Impregnation chamber 10 is preferably configured to pre-treat the cellulosic feedstock, for example by moistening and/or heating the cellulosic feedstock.

Figure 2:
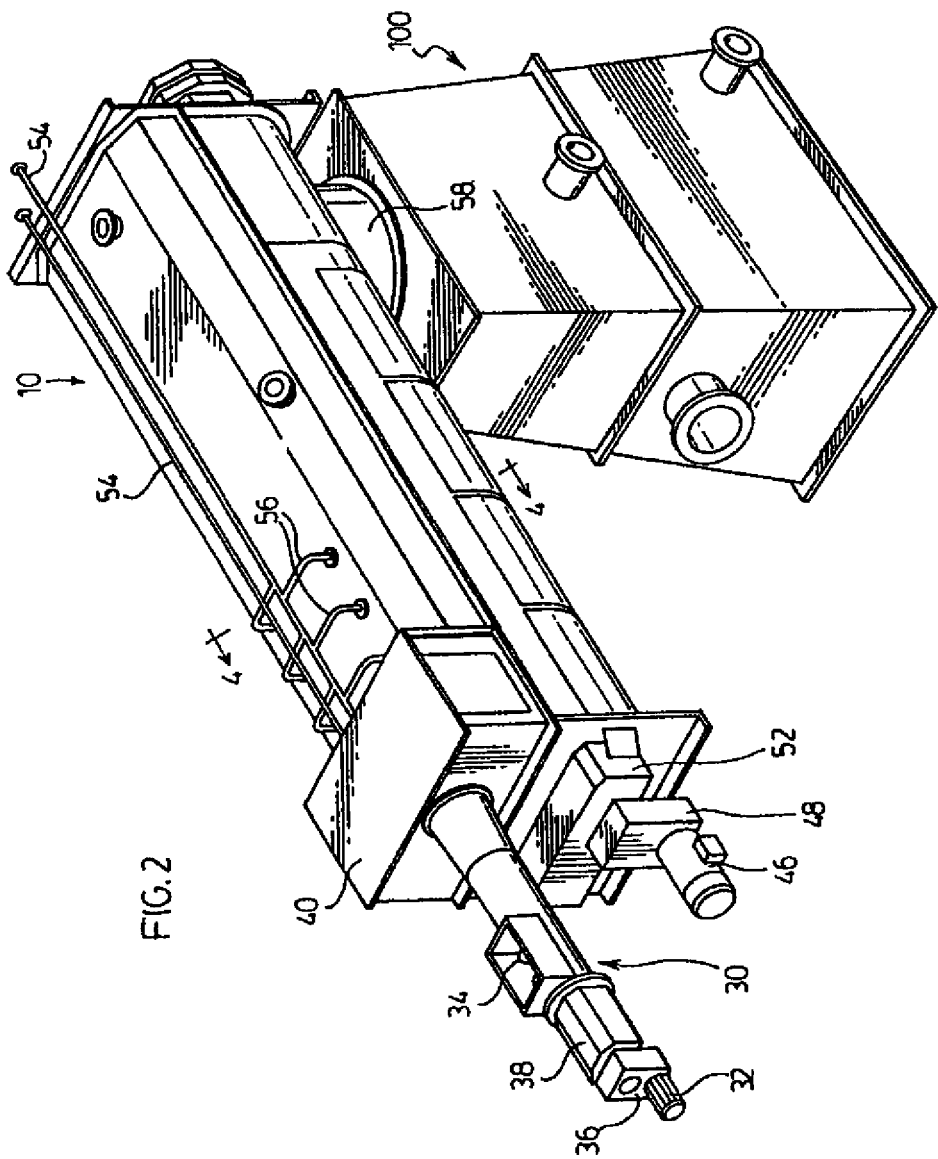
FIG. 2 is a perspective illustration of the impregnation chamber of FIG. 1.
Figure 3:
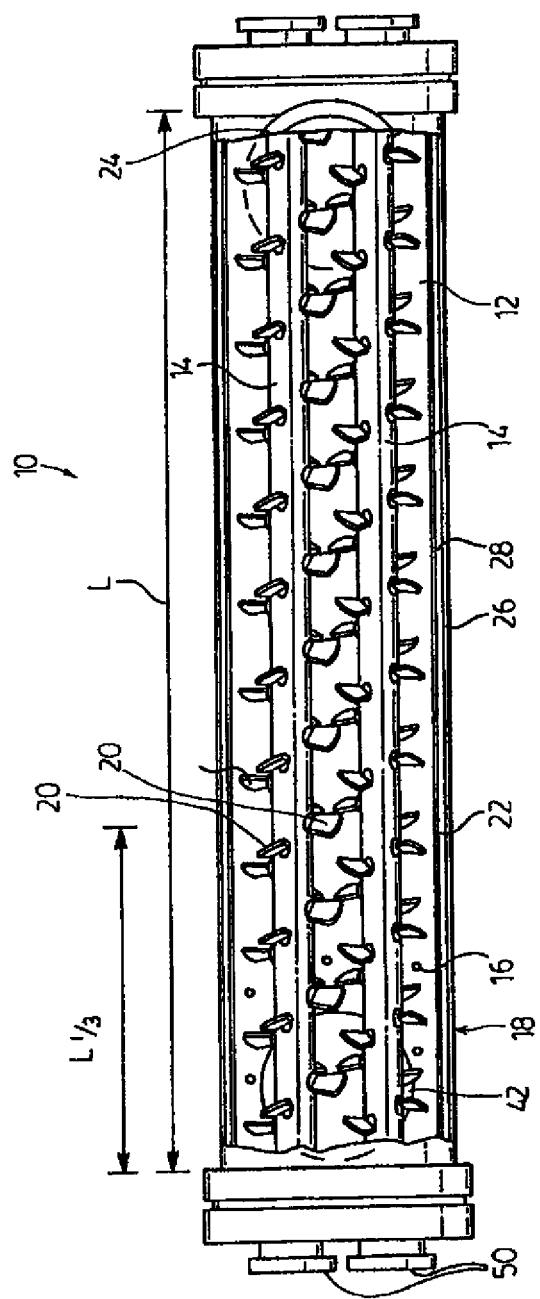
FIG. 3 is a top cutaway view of the impregnation chamber of FIG. 1.
Figure 4:
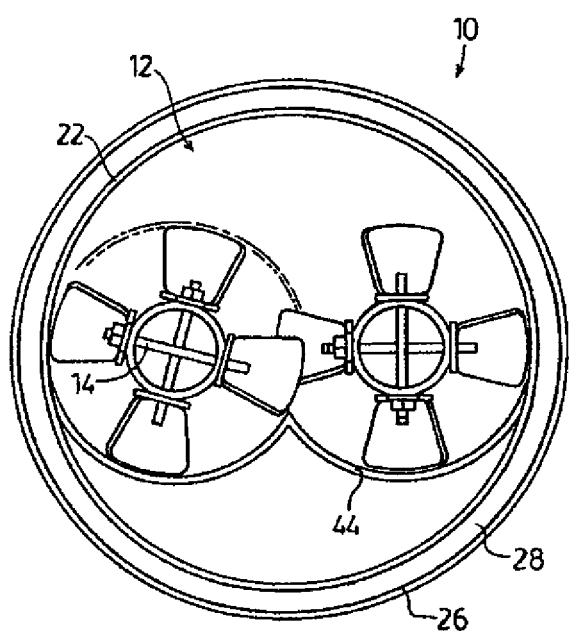
FIG. 4 is a cross section taken along line 4-4 in FIG. 2.

A preferred impregnator 10 is exemplified in FIGS. 2-4. As shown therein, in some embodiments, an impregnator feeder 30, namely a feeder that conveys feedstock into impregnation chamber 12, is preferably positioned upstream of mixing or impregnation chamber 12. Feeder 30 may be of any design. Preferably, feeder 30 is of a design that inhibits, and preferably prevents, the flow of moisture upstream of feeder 30. For example, a rotating valve or the like may be provided to segment such upstream flow. Preferably impregnation feeder is a screw feeder comprising a motor 32 drivingly connected to a screw or auger 34 positioned below an inlet, such as via a transmission or gear reduction assembly provided in housing 36. The shaft on which screw 34 is provided may be rotatably mounted in housing 38 such that augur 34 is a cantilevered plug screw conveyor. Accordingly, feeder 30 produces a plug of material that prevents upstream migration of moisture. The plug may be conveyed into inlet housing 40 that is mounted to impregnation chamber 12. The feedstock may then pass downwardly into impregnation chamber 12.

Impregnator 10 may comprise an inlet 42 positioned below inlet housing 40, one or more conveyance members 14 for urging the cellulosic feedstock along the length of chamber 12, one or more moisture injection ports 16, which may be provided on paddles 20 of conveyance member 14 and/or inner wall 22 of impregnator 10, for injecting moisture into the cellulosic feedstock, one or more heating jackets 18 provided outward of inner wall 22 for heating the cellulosic feedstock, and an outlet 18. Heating jacket 18 may comprise an outer wall 26 spaced from inner wall 22 to define a passage 28 through which a heated fluid, e.g. water, may pass.

As exemplified in FIG. 2, one or more conduits 54 may convey water to a plurality of branch conduits 56 extending to different locations on the upper portion of chamber 12. The ends of these conduits are in fluid flow communication with the interior of chamber 12, via, e.g., a moisture addition member such as a nozzle or an open ended pipe or the like.

As exemplified, conveyance members 14 are rotatably mounted in chamber 12 and are drivenly connected to a motor 46. As exemplified, motor 46 is drivingly connected to conveyance members 14 via a transmission or gear reduction assembly provided in housing 48. The gear reduction assembly may be drivingly connected to ends 50 of conveyance members 14 that are positioned inside housing 52.

In order to prevent material stagnating in impregnator 10, impregnator 10 may have a bottom wall 44 that has two or more portions each of which has a conveyance member 14 associated therewith. Bottom wall 44 and conveyance member 14 are preferably configured such that bottom wall 44 is swept as conveyance member 14 rotates. For example, as exemplified in FIG. 4, bottom wall 44 may be scallop shaped, e.g., have two inverted arches or troughs. Further details regarding various embodiments of optional mixing vessel 10 may be found in co-pending U.S. patent application Ser. No. 12/181,596, filed on Jul. 29, 2008, the disclosure of which is incorporated herein by reference in its entirety. In alternate embodiments, impregnation chamber 10 may pre-treat the cellulosic feedstock in another manner, and the invention is not limited in this regard.

After the cellulosic feedstock is optionally pre-treated in mixing vessel 10, it is directed to holding tank apparatus 100, e.g., via outlet passage 58 that is downstream from outlet 24 of chamber 12, where it is preferably held or contained for a residence time, such that for example, moisture added in mixing vessel 10 has sufficient time to penetrate into the feedstock so that the feedstock is ready for downstream processing. Alternately, or in addition, the feedstock may require additional time for all portions of the feedstock to be raised to a predetermined temperature that is suitable for downstream processing. Alternately, the feedstock entering holding tank 100 may be at the predetermined conditions for downstream processing and holding tank is used as a reservoir to hold prepared feedstock such that downstream processes may operate on a continuous basis.

In accordance with this invention, from a vessel that preferably has a downwardly extending passage for the feedstock (e.g. holding tank 100), the cellulosic feedstock is directed to one or more downstream process units, preferably hydrolysis reactors, more preferably autohydrolysis reactors followed preferably by one or more enzymatic hydrolysis reactors (not shown), positioned downstream from the holding tank apparatus 100 such that the cellulose may be hydrolyzed to produce sugars that are suitable for fermentation to ethanol.

Figure 1:
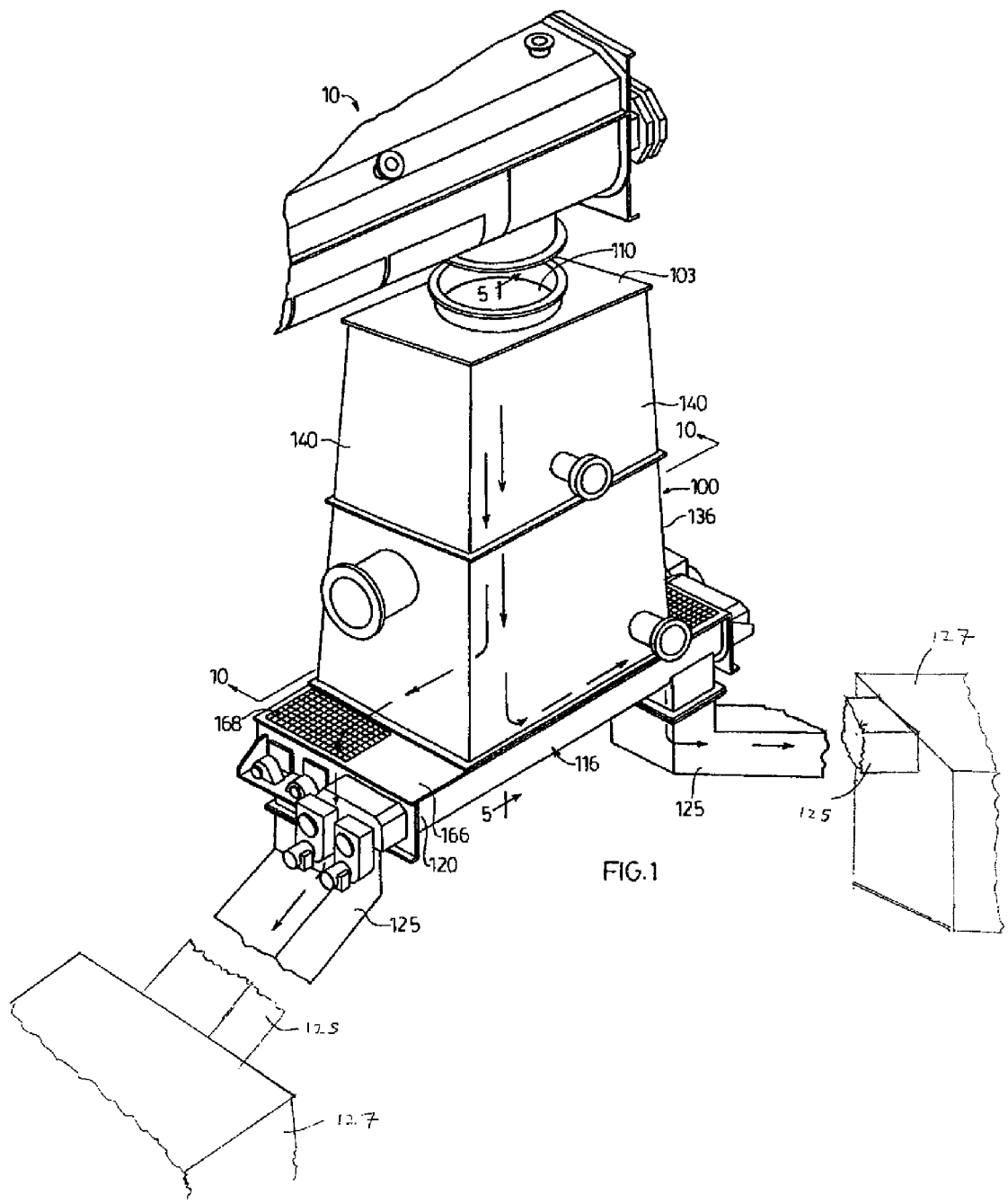
FIG. 1 is a perspective illustration of an embodiment of a holding tank of the present invention, showing impregnation chamber positioned upstream from the holding tank.
Figure 5:
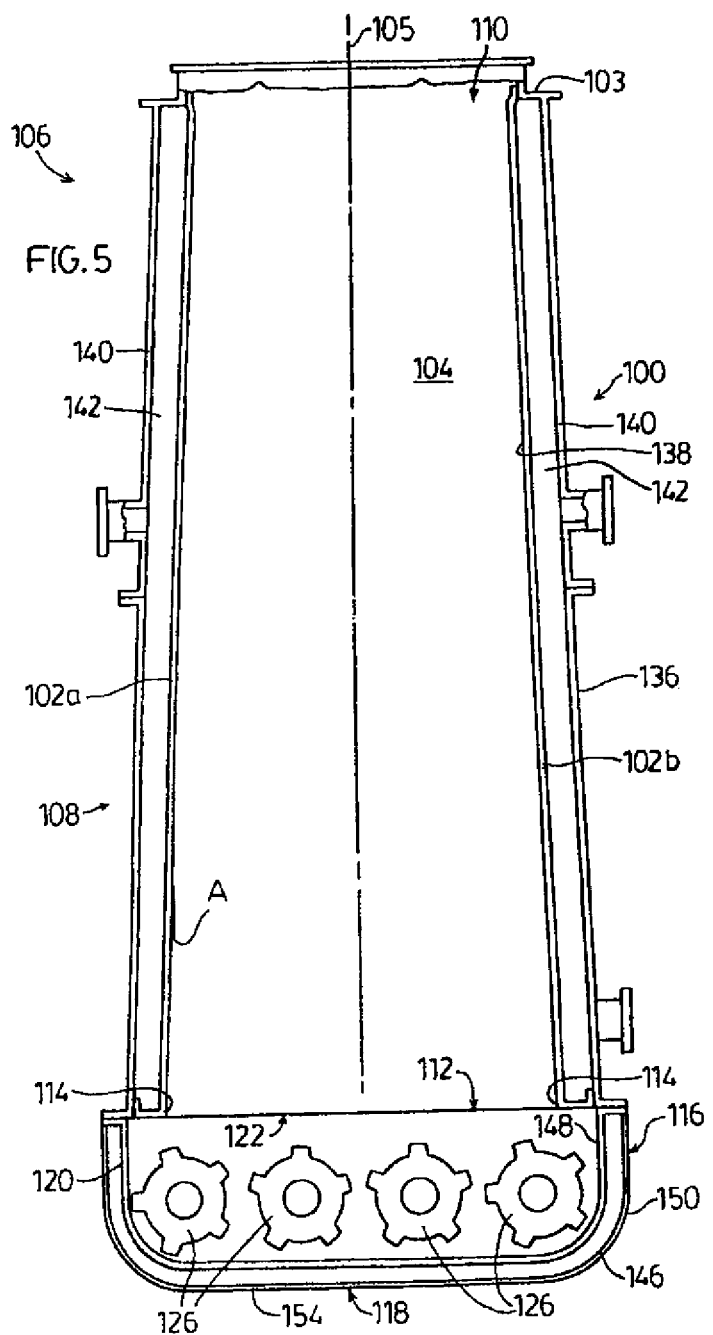
FIG. 5 is a cross section taken along line 5-5 in FIG. 1.

As exemplified in FIGS. 1 and 5, holding tank 100 is oriented such that the passage through holding tank 100 preferably extends generally downwardly and the passage therethrough is preferably configured so as to reduce, and more preferably essentially prevent, bridging of feedstock in holding tank 100. Further, the passage from impregnator 10 to holding tank 100 preferably extends generally downwardly. Accordingly, it is preferred that the passage through holding tank 100 extends generally downwardly and that the passage has a greater cross sectional area at the lower end then the upper end. More preferably, the cross sectional area continually increases in the downward direction. This may be achieved by constructing the passage of the holding tank with one or more walls that diverge in the downward direction.

If the feedstock passing downwardly through holding tank 100 interlocks, it may form a blockage by a process known as bridging. The blockage may extend all the way across the passage in holding tank 100 thereby preventing downward movement of feedstock and causing a gap in the supply of feedstock to the downstream process unit. Alternately, it may block only part of the passage. In any event, intervention would then be required to remove the blockage. The interruption of feedstock delivery to the downstream process unit could require part of a plant to be shut down while the blockage is removed thereby reducing throughput and also requiring the plant to be brought back to steady state operating conditions once the blockage is cleared. Accordingly, the holding tank may require monitoring to permit intervention at an early stage should bridging occur. By increasing the cross sectional area in the downstream direction, the tendency of the feedstock to form a blockage of the passage is reduced and may be eliminated.

Figure 10:
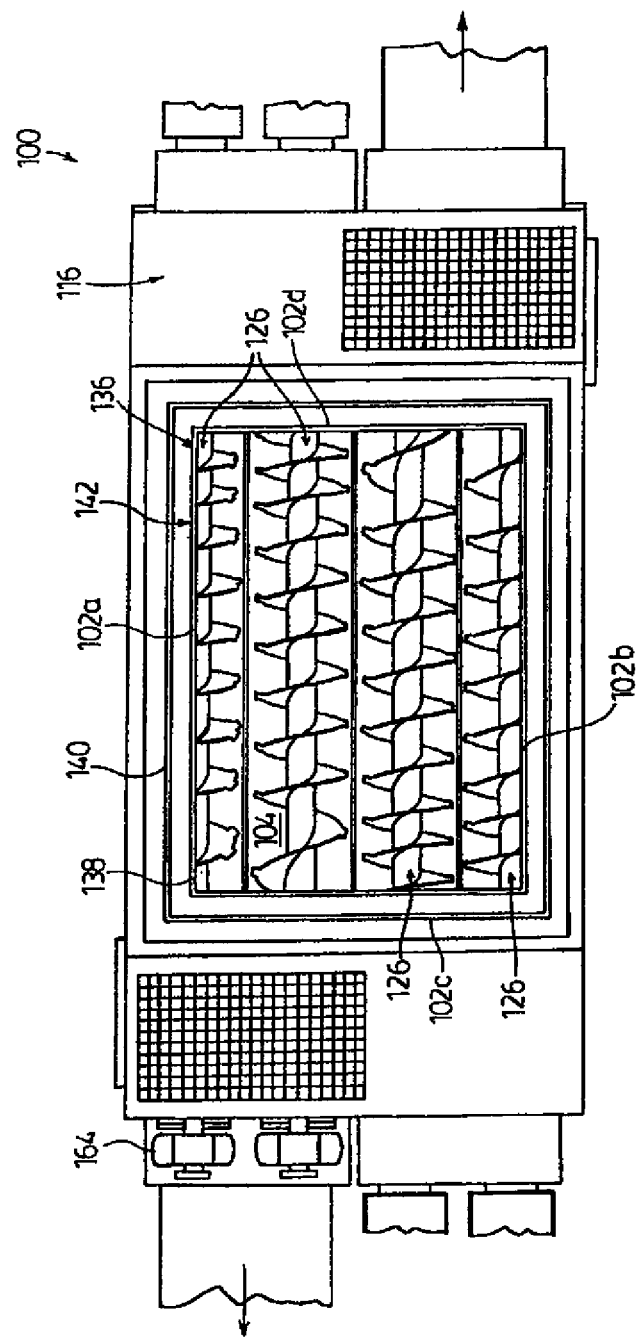

As exemplified in FIGS. 5 and 10, holding tank 100 comprises at least one sidewall 102, which defines a volume or passage 104. In the embodiment shown, holding tank apparatus 100 comprises four sidewalls, namely front wall 102a, and a spaced apart opposed rear wall 102b, and a side wall 102c, and a spaced apart opposed side wall 102d, and further comprises a top wall 103. Accordingly, passage 104, which is defined by sidewalls 102a, 102b, 102c and 102d, is rectangular in transverse section. In other embodiments, holding tank apparatus 100 may comprise, for example, a single rounded sidewall so as to have a transverse section that is circular, elliptical or the like. It will be appreciated that any other transverse section may be utilized.

Passage 104 is preferably longitudinally extending, for example along axis 105, and comprises an upper portion 106, and a lower portion 108. Passage 104 preferably extends vertically. However passage may extend generally vertically (i.e., at an angle to the vertical such that feedstock will flow downwardly therethrough under the force of gravity). In some embodiments, passage 104 may have a length along axis 105 of between about 5 ft and about 20 ft.

An inlet 110 is provided adjacent upper portion 106, and an outlet 112 is provided adjacent lower portion 108, at an elevation below the inlet 110. In the embodiment shown, inlet 110 is defined by an opening in top wall 103, and outlet 112 is defined by the lower ends 114 of sidewalls 102. It will be appreciated that inlet 110 may comprise the entirety of the top end of holding tank 100 and accordingly, a top wall 103 may not be required. It will be appreciated that in the preferred embodiment, no lower surface is provided for passage 104 and that the lower end of passage 104 is open. Accordingly, feedstock may flow downwardly through passage 104 unimpeded until it encounters feedstock stored in holding tank 100 or until it encounters housing 116. As exemplified, inlet 110 is in fluid communication with and receives cellulosic feedstock from outlet 24 of impregnation chamber 10 (e.g. it is downstream of outlet conduit 58), and outlet 112 is preferably in fluid communication with and directs cellulosic feedstock to one or more autohydrolysis reactors (not shown).

Referring still to FIG. 5, in the preferred embodiment, lower end 108 of passage 104 has a greater cross sectional area than upper end 106 of passage 104. That is, a transverse cross section taken through passage 104 adjacent outlet 112 has a greater cross sectional area than a transverse section taken through passage 104 adjacent inlet 110. For example, the cross sectional area taken adjacent outlet 112 may have an area of between about 40 ft$^2$ and about 60 ft$^2$, and the cross sectional area taken adjacent inlet 110 may have an area of between about 20 ft² and about 40 ft².

Sidewalls 102 may be configured in a variety of ways in order to provide lower end 108 with a greater cross sectional area than upper end 106. In the embodiment shown, sidewall 102a and sidewall 102b are opposed to each other, and sidewall 102c and sidewall 102d are opposed to each other, and each of the sidewalls diverge from axis 105 going from inlet 110 to outlet 112. Accordingly, passage 104 is substantially frusto-pyramidal, and lower end 108 has a greater cross sectional area than upper end 106. In an alternate embodiment, sidewalls 102a and 102b may extend substantially parallel to axis 105, and sidewalls 102c and 102d may diverge from axis 105. In yet another alternate embodiment, holding tank apparatus 100 may comprise a single rounded sidewall defining a frustoconical passage 104. In yet another embodiment, sidewalls 102 may be stepped. It is preferred that sidewalls 102 continually diverge and that they continually diverge for the entire length of passage 104 as exemplified. Preferably, they diverge at an angle A from the vertical from about 1° to about 20°, preferably from about 2° to about 5°. It will also be appreciated that inner surface 138 of sidewalls 102 are preferably smooth and clear of projections that could be a source causing bridging to occur.

Providing lower portion 108 with a greater cross sectional area than upper portion 106 may aid in preventing cellulosic material from adhering or sticking to sidewalls 102 as the cellulosic material passes through holding tank apparatus 100. Accordingly, each portion of cellulosic feedstock that passes through holding tank 100 may have essentially the same residence time in passage 104.

In alternate embodiments, lower portion 108 of passage 104 may not have a greater cross sectional area than upper portion 106 of passage 104. For example, each of sidewalls 102 may extend essentially vertically and parallel to each other.

In accordance with this invention, after traveling through passage 104, the feedstock is conveyed laterally (transverse to axis 105). Further, it is preferred that the feedstock is actively withdrawn from holding tank 104 instead of permitting the feedstock to passively exit therefrom. Accordingly holding tank 100 may further comprise or be provided with at least two conveyors adjacent outlet 112 that are configured to actively convey the cellulosic feedstock laterally across outlet 112 to withdraw the cellulosic feedstock from passage 104. Referring to FIGS. 5 to 8, in the embodiment shown, each conveyor comprises a plurality of screw conveyors 126 (e.g., two), which are housed in a housing or discharge unit 116. The conveyor may be any transport mechanism known in the art to transport, and preferably actively transport, feedstock laterally from outlet 112. For example, the conveyor may comprise an auger, a screw conveyor, tabbed flight screw with bars, a belt conveyor or the like that extends transversely to axis 105.

In the embodiment shown, housing 116 comprises a base 118, sidewalls 120, and an open top 122. Open top 122 is preferably at least as large as outlet 112, and is in vertical registration with outlet 112, such that material passing through outlet 112 may pass directly downwardly through open top 122. Accordingly, all of outlet 112 is exposed to the conveyors 132 in housing 116. It will be appreciated that in alternate embodiments, sidewalls 102 of passage 104 may provide the sidewalls of housing 116. That is, sidewalls 102 may extend beyond outlet 112. Accordingly, in such an embodiment, outlet 112 of passage 104 may not be defined by ends 114 of sidewalls 102, and rather, may be defined by a portion of sidewalls 102 above ends 114.

Housing 116 comprises at least first and second housing outlets 124a, 124b, through which cellulosic feedstock conveyed by screw conveyors 126 exits housing 116. Cellulosic feedstock exiting housing outlet(s) 124a, 124b may pass into two or more conduits 125, which may, for example, lead to two or more, e.g., autohydrolysis reactors 127 (see FIG. 1). Accordingly, outlet 124a may be coupled to a first conduit 125, which leads to a first hydrolysis reactor 127, and outlet 124b may be coupled to a second conduit 125, which leads to a second hydrolysis reactor 127.

Preferably each conduit 125 is provided with one or more screw conveyors or the like extending in the direction of conduit 125. An advantage of having more then one outlet 124a, 124b is that two treated feedstock streams may be provided from holding tank 100, each of which may be fed to a different downstream process vessel, e.g. a different steam explosion reactor.

Figure 6:
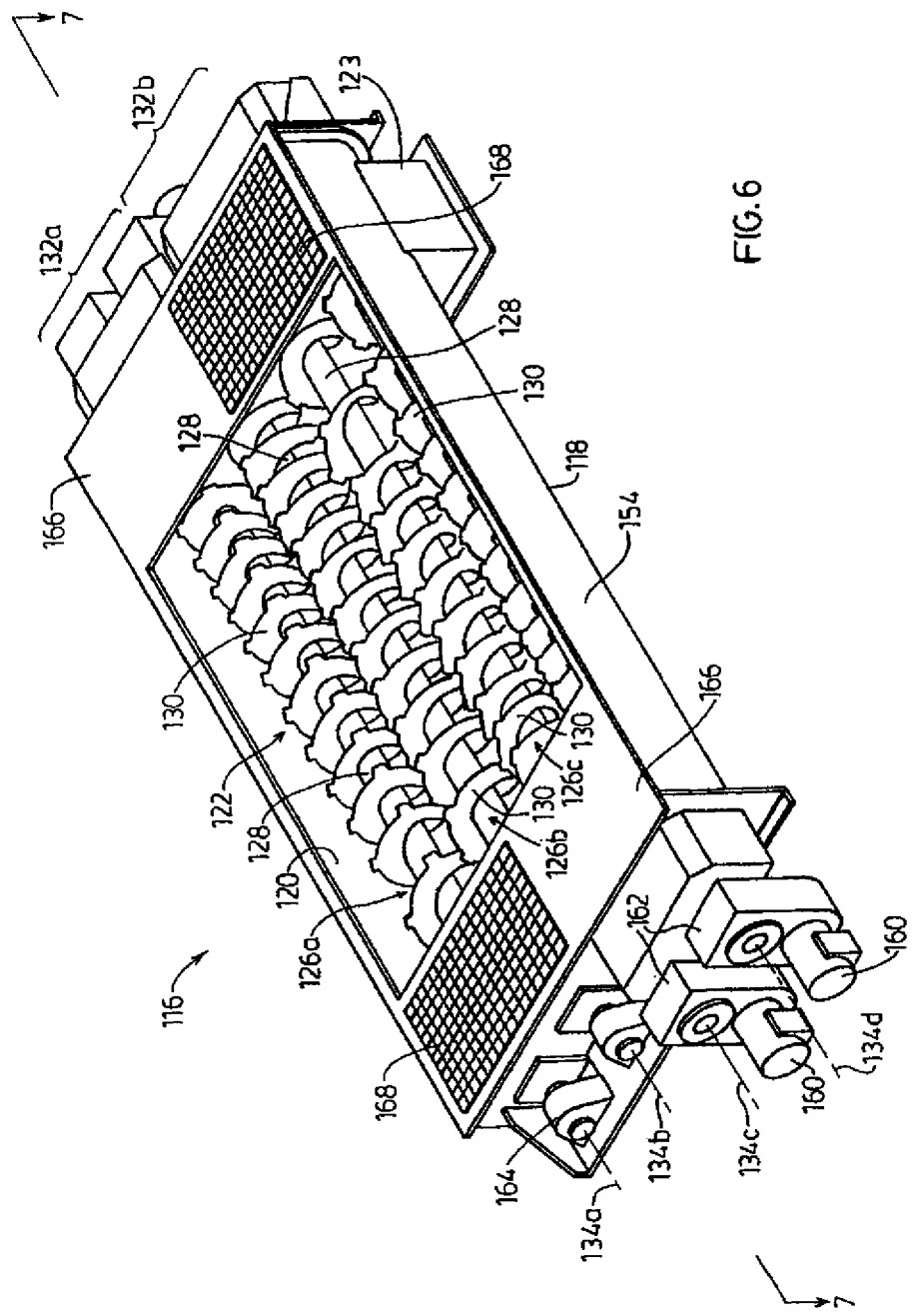
FIG. 6 is a perspective view of an embodiment of a housing of the an discharge unit in accordance with an embodiment of the present invention, shown removed from a holding tank.
Figure 7:
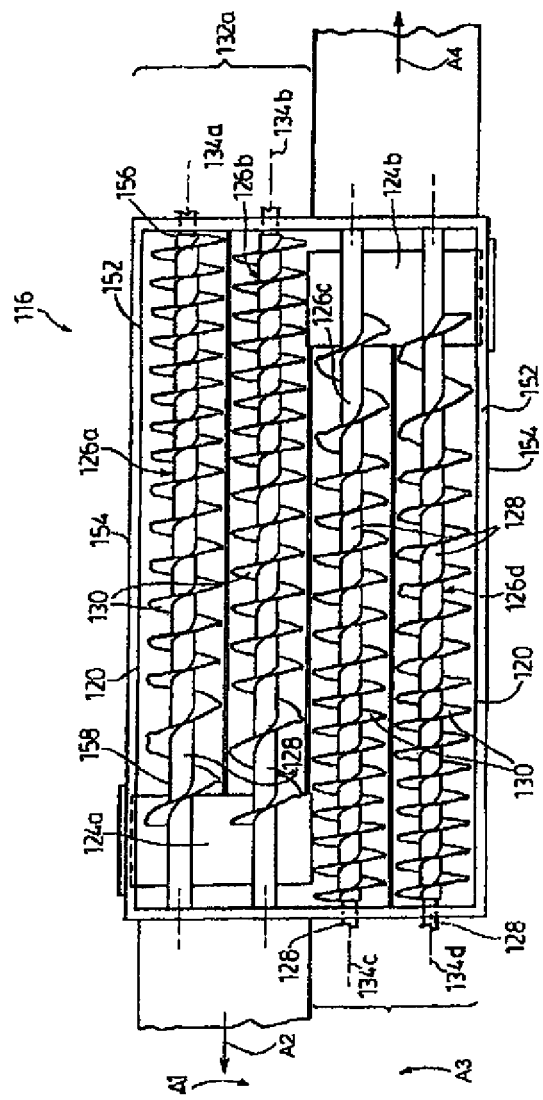
FIG. 7 is a cross-section taken along line 7-7 in FIG. 6.
Figure 8:
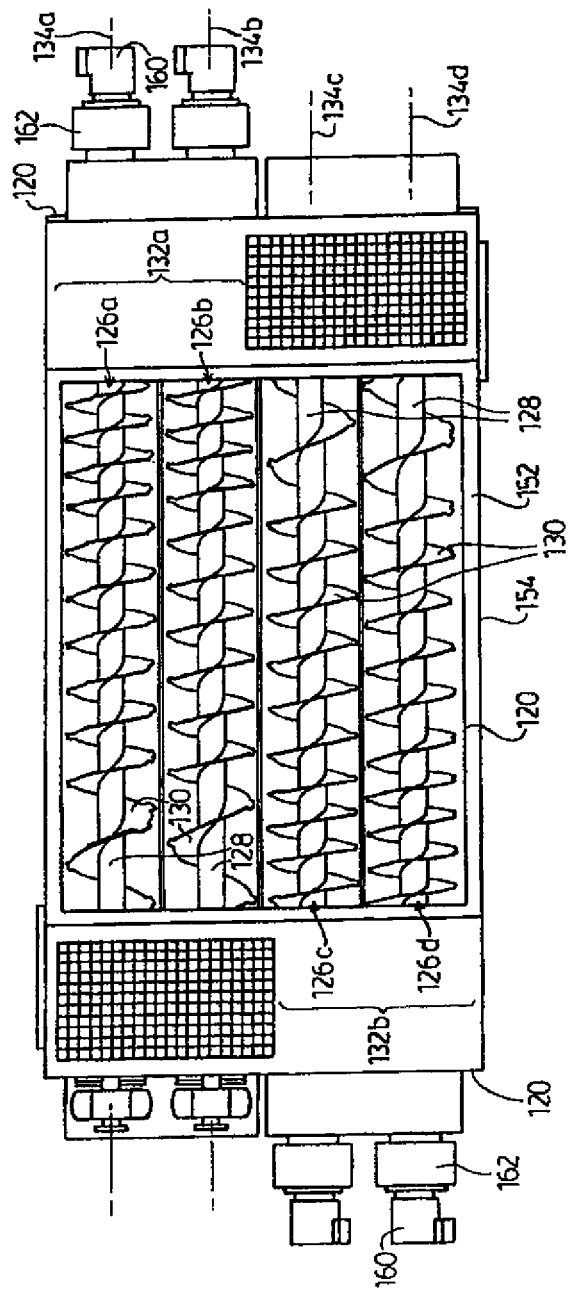
FIG. 8 is a top view of the housing of FIG. 6.
Figure 9:
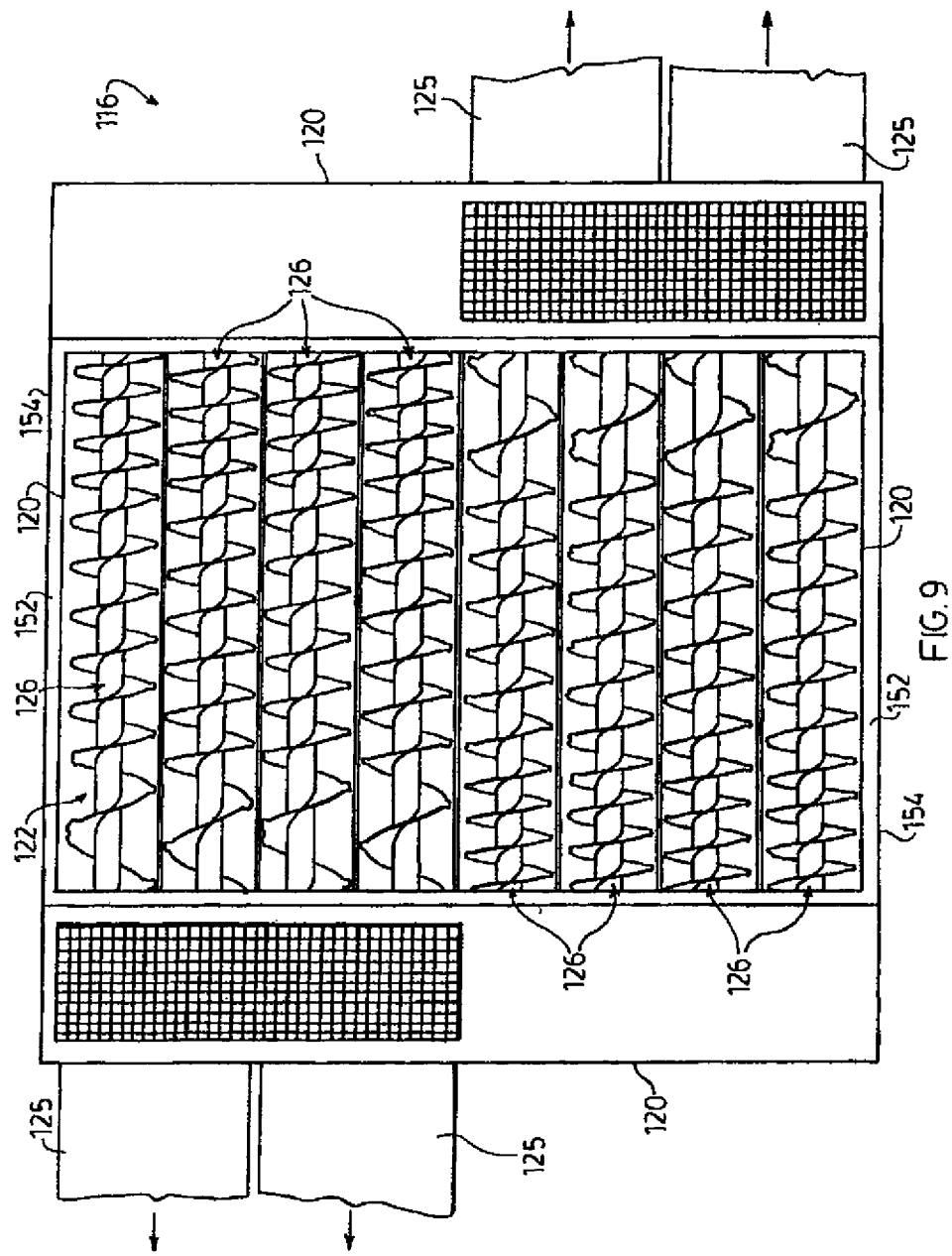
FIG. 9 is a top view of an alternate embodiment of a housing of the present invention; and, FIG. 10 is a cross-section taken along line 10-10 in FIG. 1.

As exemplified, housing 116 comprises two housing outlets 124a, 124b defined in base 118 (see FIG. 7). Preferably, each outlet 124 is positioned such that it is not underneath passage 104 (laterally spaced from passage 104). An advantage of positioning outlets 124 laterally from passage 104 is that feedstock may be withdrawn from all of outlet 112 and, more preferably, evenly from across outlet 112. Further, housing outlets 124a and 124b are preferably positioned on opposite sides of housing 116. Accordingly, housing outlets 124a and 124b may direct cellulosic material to two different, e.g., autohydrolysis reactors, positioned on opposite sides of holding tank 100. As exemplified in FIGS. 1 and 6, housing 116 may have upper wall 166 that extends over the portion of housing 116 positioned laterally of holding tank 100. Top wall 166 may cover the portion of screw conveyor 126 positioned laterally of holding tank 100. Optionally, a grate 168, or other member that provides a window, may be position in top wall 166 above outlet 124. Grate 168 permits a worker to observe the travel of feedstock into conduits 125.

As exemplified, the screw conveyors 126 are mounted above base 118, and each screw conveyor extends transversely to axis 105 across all of outlet 112 (i.e. the length L of each screw conveyor extends at least from a first side of outlet 112 to a second side of outlet 112). Each screw conveyor 126 comprises a shaft 128 and at least one helical flight 130 extending about the shaft, and is configured to rotate to engage material exiting outlet 112, and to convey it towards one of the housing outlets 124. Shaft 128 may be rotatably mounted by any means known in the art. As exemplified, shaft 128 has one end journalled in a bearing housing 164 and a second end journalled in a transmission housing 162.

In the embodiment shown, housing 116 comprises four screw conveyors 126, which are arranged in pairs. Each pair comprises two adjacent screw conveyors 126 which convey the cellulosic feedstock in the same direction towards a common housing outlet 124. In the embodiment shown, first pair 132a comprises screw conveyors 126a and 126b, which rotate about respective first 134a and second 134b generally parallel axes, and second pair 132b comprises screw conveyors 126c, and 126d, which rotate about respective first 134c and second 134d generally parallel axes. Each of axes 134 are preferably horizontal, but may be at an angle of up to 45° or greater from the horizontal. Accordingly, screw conveyors 126a and 126b transport treated feedstock to outlet 124a and screw conveyors 126c and 126d transport treated feedstock to outlet 124b, which is on an opposed side to outlet 124a. It will be appreciated that screw conveyors 126a, 126b, 126c and 126d extend under essentially all of outlet 112. Therefore, the screw conveyors 126 preferably withdraw treated feedstock for all portions of outlet 112. Alternately, or in addition, each outlet 124 may have one or more screw conveyors 126 or other transport member associated therewith.

Referring still to FIG. 7, as exemplified, screw conveyors 126a and 126b of first pair 132a may each be rotated in a direction indicated by arrow A1, to feed material from above in a direction indicated by arrow A2 towards housing outlet 124a. Further, screw conveyors 126c and 126d of second pair 132b may each be rotated in a direction indicated by arrow A3, to feed material from above in a direction indicated by arrow A4 towards housing outlet 124b.

In order to permit each screw conveyor 126 to be rotated in a particular direction of rotation, each screw conveyor may be driven by its own drive motor 160. As shown in FIGS. 6 and 7, each shaft 128 extends outwardly past sidewall 120 into a transmission housing 162 wherein motor 160 is drivingly connected to shaft 128. Any driving linkage known in the art may be used. It will be appreciated that in an alternate embodiment, two or more shafts may be driven by a single motor 160.

Accordingly, as exemplified, housing outlets 124a and 124b are positioned on laterally opposite sides of housing 116, and each helical flight 130 is right-handed. Accordingly, direction A1 and direction A3 are opposite to each other, and directions A2 and A4 are opposite to each other. However, in alternate embodiments, housing outlets 124a and 124b may be positioned on the same lateral side as each other. In such an embodiment, directions A1 and A3 may be substantially the same, and directions A2 and A4 may be substantially the same. In yet further alternate embodiments, the helical flight 130 of the first pair 132a of screw conveyors 126a, 126b, may be right handed, and the helical flight 130 of the second pair 132b of screw conveyors 126c, 126d may be left handed. Accordingly, in such an embodiment, directions A1 and A3 may be the same, and direction A2 and A4 may be opposite. It will be appreciated that each pair of screw conveyors 126 may be configured such that they rotate in opposite directions. For example, screw conveyor 126a may be configured to rotate clockwise and screw conveyor 126b may be configured to rotate counterclockwise.

It will be appreciated that in alternate embodiments, one or more screw conveyors 126 may be otherwise configured. For example, housing 116 may comprise a plurality of screw conveyors, which are not arranged in pairs (e.g. the screw conveyors may arranged in sets of three, or as single screw conveyors), or housing 116 may comprise more than two pairs of screw conveyors. For example, in an alternate embodiment shown in FIG. 9, holding tank 100 comprises four housing outlets 124, and four pairs 132 of screw conveyors 126.

Referring still to FIGS. 5-7, at least one of the screw conveyors 126, and preferably all of the screw conveyors 126, may have a variable pitch along its length. That is, the pitch of helical flight 130 is not constant along the length L of at least one of the screw conveyors 126.

For example, in the embodiments shown, each screw conveyor has a first end 158 proximal to its respective housing outlet 124 (i.e. the outlet towards which it conveys cellulosic feedstock), and a second end 156 distal to its respective housing outlet 124 (shown in FIG. 7). The pitch of helical flight 130 at first end 158 is greater or wider than the pitch of helical flight 130 at second end 156. For example, the pitch at the first end may be between about 14 inches and about 88 inches, and the pitch at the second end may be between about 4 inches and about 8 inches.

In the embodiments shown, the pitch of each helical flight 130 varies continuously, and preferably at a constant rate, between the first end 158 and the second end 156. That is, the pitch gradually becomes wider towards each discharge member outlet 124. In alternate embodiments, an abrupt transition between wider and narrower regions of flight may occur. For example, each screw conveyor may have a first region extending from first end 158 towards a mid-point of screw conveyor 126, and a second region extending from second end 156 towards the midpoint. The first region may have a first range of pitch and the second region may have a second range of pitch. For example, the first range of pitch may be between about 14 inches and about 18 inches, and the second range of pitch may be between about 4 inches and about 8 inches. In yet another embodiment, each screw conveyor may comprise an intermediate region between the first region and the second region, and the intermediate region may have a third range of pitch that is less than the first range of pitch and more than the second range of pitch. For example, the third range of pitch may be between about 6 inches and about 10 inches.

Preferably, the screw conveyors 126 of each pair 132 have the same pitch at any location along their lengths. That is, the helical flight of screw conveyors 126a and 126b is essentially identical, and the helical flight of screw conveyors 126c and 126d is essentially identical.

Furthermore, the pitch of a first pair of screw conveyors is preferably a mirror image of the pitch of a second pair of screw conveyors, which convey the cellulosic feedstock in a direction opposite to the first pair of screw conveyors. That is, the pitch of screw conveyors 126a and 126b, which convey cellulosic material in direction A2, is a mirror image of the pitch of screw conveyors 126c and 126d, which convey cellulosic material in a direction A4.

Providing each screw conveyor with a variable pitch, and more specifically with a narrower pitch distal to the housing outlet permits more equal amounts, and may allow for substantially equally amounts of cellulosic feedstock to be withdrawn from each portion of outlet 112. That is, material deposited in screw conveyor 126 at the distal end 156 will be conveyed towards the respective outlet 124 for that screw conveyor. As that material is transported laterally, the pitch of the screw increases permitting additional material to be deposited directly in the screw conveyor from outlet 112. Further increases in the pitch will permit additional portions of the material to fall into screw conveyor. The portion or portions of the screw conveyor closer to outlet 124 (in the direction of transport) has a wider pitch such that it may accommodate material conveyed from the distal region, as well as material deposited directly thereon from passage 104. Accordingly, feedstock is withdrawn from across all of outlet 112.

Referring to FIGS. 5 and 10, vessel 100 (e.g., the holding tank) preferably further comprises a heating jacket 136 provided on at least a portion of vessel 100. Preferably, the at least one sidewall 102 is provided with a heating jacket. For example, in the embodiment shown, heating jacket 136 surrounds all of each sidewall 102. Heating jacket 136 may comprise a plurality of outer walls that are generally parallel to and spaced from sidewalls 102 so as to define an enclosure 142 therebetween. A fluid may be passed through enclosure 142 from an inlet (not shown) to an outlet (not shown) so that a heated fluid is passed through enclosure 142. Heating jacket 136 may be of any construction known in the art. Accordingly, the cellulosic material may be heated to a predetermined temperature, or maintained at a predetermined temperature as it passes through vessel 100.

Referring to FIG. 5, in a further preferred embodiment, housing 116 also or alternately may comprise a second heating jacket 146 provided by housing 116. In the embodiment shown, heating jacket 146 is configured similarly to heating jacket 136, and may comprise an outer wall 154 spaced outwardly from sidewalls 120 and/or base 118 and is configured for passing a heated fluid through an enclosure 150 defined between outer walls 154 and sidewalls 120 and/or base 118. Heating jacket 146 may be of any construction known in the art.

In some embodiments, one or more temperature sensors may be provided in passage 104. For example, a first thermocouple (not shown) may be provided in the upper portion 106 of passage 104, to measure the temperature of the cellulosic feedstock entering inlet 110, and a second thermocouple (not shown) may be provided in the lower portion 108 of passage 104, to measure the temperature of the cellulosic feedstock exiting outlet 112. In some embodiments, one or more displays (not shown) may be coupled to the one or more temperature sensors, such that a user may view the measured temperatures, and optionally, adjust the amount of heat provided to holding tank 100 based on the measured temperatures. In further embodiments, the one or more sensors may be coupled to a processor, which may automatically adjust the amount of heat provided to holding tank 100 based on the measured temperatures.

A method of treating a cellulosic feedstock that may be used for ethanol production will now be described. Although the method will be described with reference to holding tank 100, it will be appreciated that the method may be carried out using an alternate apparatus, and discharge housing 116 may be operated utilizing alternate conveyors.

A suitable cellulosic feedstock is preferably first subjected to moisture impregnation to raise the moisture content of the feedstock to a predetermined level prior to entry to the discharge housing 116, and preferably prior to entry to holding tank 100. Preferably, the moisture content of the feedstock upon entry to the holding tank or discharge housing 116 is from about 30 wt % to about 60 wt %, preferably from about 45 wt % to about 55 wt %. The cellulosic feedstock may be obtained from, for example, a pre-treatment device such as impregnator 10, in which moisture is added to the cellulosic feedstock to raise the moisture content from, e.g., less than about 15% to between about 30% and about 60 wt % upon entry to the holding tank. Preferably, the moisture content is between about 45 wt % and about 55 wt % upon entry to the holding tank.

The cellulosic feedstock is passed from the outlet of the impregnator 10 to the inlet of a passage upstream of discharge housing 116, e.g., holding tank 100. For example the cellulosic feedstock may be passed from outlet 18 of impregnator 10, into inlet 110 of holding tank 100.

The cellulosic feedstock, with or without being subjected to impregnation, is then preferably passed downwardly through the vessel. For example, referring to holding tank 100, inlet 110 is disposed at an elevation above outlet 112. Accordingly, the material may migrate downwardly from the inlet towards the outlet under the force of gravity. Furthermore, in embodiments wherein lower portion 108 has a greater cross sectional area than upper portion 106, the material will further migrate laterally as it migrates downwardly.

The feedstock is withdrawn from the vessel and directed towards two downstream process units. Accordingly, the feedstock obtained from the vessel is divided into two or more process streams, some, or each or which, may be travel in a different direction. At least two streams are obtained and provided to at least two different downstream process units, preferably hydrolysis reactors. The downstream process units may be operated on a batch or semi batch basis and may be operated out of phase. Accordingly, one batch hydrolysis reactor may be operated while a second batch hydrolysis reactor is filled with the cellulosic feedstock. Preferably, the cellulosic feedstock is conveyed laterally across the outlet of the vessel, and preferably in different directions.

Preferably a generally constant residence time is maintained in the holding tank. That is, the holding tank is preferably operated continuously at steady state conditions, such that all parts of each portion or layer of feedstock added at inlet 110 pass downwardly to outlet 112 at about the same rate. This result may be achieved by withdrawing feedstock from all portions of the outlet 112. For example, the material may be removed from the outlet by operating one or more screw conveyors, such as screw conveyors 126 described hereinabove, such that feedstock from all parts of the outlet 112 (e.g., all of the same horizontal layer of feedstock in the outlet 112) are collected concurrently in the screw conveyor and transported to an outlet or downstream passage. It will be appreciated that the amount of material that is withdrawn from each part of the holding tank outlet may be varied by adjusting the pitch of the flight of the screw conveyor. By enlarging the pitch at certain locations, the amount of feedstock withdrawn at those locations may be increased.

It will be appreciated that, in use, there may be an initial start up phase, wherein material is not removed from the vessel, and the vessel is filled with cellulosic feedstock from impregnation chamber 12.

The residence time may be up to 60 minutes. Preferably, the residence time is between 10 minutes and 30 minutes. An advantage of this method is that a generally uniform residence time of the feedstock in the vessel may be achieved. For example, the variance of the residence time may be up to 5 minutes, preferably, less than 3 minutes and more preferably less than 2 minutes.

In some embodiments, the cellulosic feedstock is conveyed laterally across the outlet of the holding tank, preferably in different directions, to obtain the at least two streams. For example, at least two conveying devices may be utilized to convey a first portion of the cellulosic feedstock laterally in a first direction to obtain a first steam, and at least two conveying devices may be utilized to convey a first portion of the cellulosic feedstock laterally in a second direction to obtain a second stream. For example, the holding tank may comprise a first conveyor 132a, comprising first 126a and second 126b conveying devices and a second conveyor 132b comprising third 126c and fourth 126d conveying devices, as described hereinabove. The first and second conveying devices may be configured to convey a first portion of the cellulosic feedstock laterally across the at least one outlet in a first lateral direction to obtain the first stream, and the third and fourth conveying devices may be configured to convey a second portion of the cellulosic feedstock laterally across the at least one outlet in a second lateral direction to obtain the second stream. Accordingly, the cellulosic feedstock for the first stream is drawn from a first portion of the outlet, and the cellulosic feedstock for the second stream is drawn from a second portion of the outlet.

In some embodiments, the first stream may be conveyed towards a first conduit, for example towards conduit 125 via discharge outlet 124a, and conveying the second stream towards a second conduit, for example towards conduit 125 via discharge outlet 125b.

The at least two streams are then fed into different process units, e.g., hydrolysis reactors 127. For example one conduit 125 may lead towards a first hydrolysis reactor, and a second conduit 125 may lead to a second hydrolysis reactor. The hydrolysis reactors may be, for example, autohydrolysis reactors, or acid hydrolysis reactors. Preferably, the first and second hydrolysis reactors are operated on a batch basis, and are operated out of phase with each other. For example, the first conveyor of the holding tank may be engaged to fill the first hydrolysis reactor, while the second conveyor is at rest. When the first hydrolysis reactor has been filled to a desired level, operation of the first conveyor may be stopped, and first the hydrolysis reactor may be engaged, for example by adding enzymes. While the first hydrolysis reactor is operated, the second conveyor may be engaged in order to fill the second hydrolysis reactor.

In some embodiments, the method further comprises maintaining a temperature in the holding tank between about 50° C. and about 75° C. For example, the holding tank may be optionally provided with a heating jacket, such as heating jacket 136 and/or discharge member 116 may be optionally provided with a heating jacket 146. The heating jacket may serve to heat the walls of the holding tank and/or the discharge member, such that the material within the holding tank is maintained at or raised to a temperature between 50° C. and about 75° C.

It will be appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

We claim:

1. An apparatus for use in preparing a cellulosic feedstock for ethanol production, comprising:
   (a) one or more sidewalls defining a passage extending in a downward direction having an upper portion and a lower portion;
   (b) at least one inlet adjacent the upper portion, the inlet having a cross sectional area;
   (c) at least one outlet adjacent the lower portion, the outlet having a cross sectional area wherein the cross sectional area of the outlet is greater than the cross sectional area of the inlet, and wherein one or more sidewalls diverge in the downward direction;
   (d) at least a first conveyor proximate the at least one outlet configured to convey a first portion of the cellulosic feedstock laterally across the at least one outlet in a first direction to a first conduit that is upstream of a first hydrolysis reactor; and,
   (e) at least a second conveyor proximate the at least one outlet configured to convey a second portion of the cellulosic feedstock laterally across the at least one outlet in a second direction to a second conduit that is upstream of a second hydrolysis reactor.

2. The apparatus of claim 1, wherein the first and second conveyors are positioned adjacent each other.

3. The apparatus of claim 1, wherein the first conveyor conveys cellulosic feedstock towards an outlet of the first conveyor, and the second conveyor conveys cellulosic feedstock towards an outlet of the second conveyor.

4. The apparatus of claim 1, wherein the first direction is generally opposite to the second direction.

5. The apparatus of claim 1, wherein all of the outlet is exposed to the conveyors.

6. The apparatus of claim 1, wherein the conveyors are provided in a housing having at least one conveyor outlet in a lower surface thereof for each conveyor.

7. The apparatus of claim 1, wherein each conveyor comprises at least one rotatably mounted helical screw.

8. The apparatus of claim 1, wherein each conveyor comprises at least two helical screws that are rotatable in the same direction.

9. The apparatus of claim 1, wherein each conveyor comprises at least one rotatably mounted helical screw having a variable pitch.

10. The apparatus of claim 1, further comprising a housing for the conveyors and a heating jacket disposed at least partially around the housing.

11. The apparatus of claim 1 wherein the cross sectional area continually increases from the inlet to the outlet.

12. The apparatus of claim 1 wherein the cellulosic feedstock is a moisture impregnated feedstock.

13. The apparatus of claim 12 wherein the moisture impregnated feedstock has a moisture content of between about 30 wt. % and about 60 wt. %.

* * * * *